(12) United States Patent
Trambitas et al.

(10) Patent No.: US 12,735,379 B2
(45) Date of Patent: Sep. 15, 2026

(54) COMPOSITIONS COMPRISING N-NONANOIC ACID ESTERS OF XYLITAN AND/OR SORBITAN

(71) Applicant: Evonik Operations GmbH, Essen (DE)

(72) Inventors: Alexandra Trambitas, Alzenau (DE); Jan Marian von Hof, Bochum (DE); Dominik Schuch, Duesseldorf (DE); Silvia Jentsch, Bad Soden-Salmuenster (DE); Stefan Julian Liebig, Duesseldorf (DE); Konrad Grygiel, Dortmund (DE)

(73) Assignee: Evonik Operations GmbH, Essen (DE)

( * ) Notice: Subject to any disclaimer, the term of this patent is extended or adjusted under 35 U.S.C. 154(b) by 296 days.

(21) Appl. No.: 18/570,395

(22) PCT Filed: May 30, 2022

(86) PCT No.: PCT/EP2022/064532
§ 371 (c)(1),
(2) Date: Dec. 14, 2023

(87) PCT Pub. No.: WO2022/263150
PCT Pub. Date: Dec. 22, 2022

(65) Prior Publication Data

US 2024/0287412 A1 Aug. 29, 2024

(30) Foreign Application Priority Data

Jun. 18, 2021 (EP) .................................... 21180241

(51) Int. Cl.
*C11D 1/00* (2006.01)
*C07C 69/33* (2006.01)
(Continued)

(52) U.S. Cl.
CPC ........... *C07C 69/33* (2013.01); *C07D 307/20* (2013.01); *C11D 3/0036* (2013.01); *C11D 3/221* (2013.01); *C12P 7/6454* (2013.01)

(58) Field of Classification Search
CPC ........... C11D 1/00; C11D 3/2093; C11D 3/22; C11D 3/221; C11D 3/226; C07D 307/20
See application file for complete search history.

(56) References Cited

U.S. PATENT DOCUMENTS 4,297,290 A 10/1981 Stockburger
4,861,513 A 8/1989 Lueders et al.
(Continued)

FOREIGN PATENT DOCUMENTS

CN 112778242 A 5/2021
EP 0 280 780 9/1988
(Continued)

OTHER PUBLICATIONS

Bock et al., "Carbon-13 Nuclear Magnetic Resonance Spectroscopy of Monosaccharides", Advances in Carbohydrate Chemistry and Biochemistry, vol. 41, pp. 27-66, 1983.
(Continued)

*Primary Examiner* — Brian P Mruk
(74) *Attorney, Agent, or Firm* — Grüneberg Global IP, PLLC

(57) ABSTRACT

Compositions are made with n-nonanoic acid esters of xylitan and/or sorbitan. A method to produce these compositions is developed. Further formulations are prepared with the compositions, and a method of improved dishwashing with the compositions is developed.

20 Claims, 1 Drawing Sheet

| | Reference formulation 1 | Reference formulation 2 | Test formulation 1 |
|---|---|---|---|
| Image of an exemplary Test Monitor for the test series | | | |

(51) Int. Cl.

| | |
|---|---|
| ***C07D 307/20*** | (2006.01) |
| ***C11D 3/00*** | (2006.01) |
| ***C11D 3/22*** | (2006.01) |
| ***C12P 7/6454*** | (2022.01) |

(56) References Cited

U.S. PATENT DOCUMENTS

| | | | | |
|---|---|---|---|---|
| 8,222,438 | B2 | 7/2012 | Bastioli et al. | |
| 8,642,525 | B2 | 2/2014 | Herrwerth et al. | |
| 8,846,962 | B2 | 9/2014 | Bieser et al. | |
| 9,272,975 | B2 | 3/2016 | Bieser et al. | |
| 11,491,093 | B2 | 11/2022 | Brandt et al. | |
| 2012/0015893 | A1 * | 1/2012 | Herrwerth | A61Q 5/12 514/23 |
| 2020/0375862 | A1 * | 12/2020 | Brandt | A61K 8/375 |
| 2021/0283037 | A1 * | 9/2021 | Denda | A61K 8/345 |
| 2023/0023141 | A1 | 1/2023 | Von Hof et al. | |
| 2023/0033620 | A1 | 2/2023 | Liebig et al. | |
| 2023/0055814 | A1 | 2/2023 | Von Hof et al. | |
| 2024/0270676 | A1 | 8/2024 | Liebig et al. | |
| 2024/0287412 | A1 | 8/2024 | Trambitas et al. | |

FOREIGN PATENT DOCUMENTS

| | | | | |
|---|---|---|---|---|
| EP | 2 410 979 | | 2/2012 | |
| EP | 3 744 310 | | 12/2020 | |
| EP | 3 839 052 | | 6/2021 | |
| JP | 9-95468 | A | 4/1997 | |
| JP | H0995468 | * | 4/1997 | C11D 1/66 |
| JP | 2012-521380 | A | 9/2012 | |
| JP | 5688318 | | 3/2015 | |
| WO | 2007/039481 | | 4/2007 | |
| WO | 2008/123453 | A1 | 10/2008 | |
| WO | 2010/108738 | | 9/2010 | |
| WO | 2011/080296 | | 7/2011 | |
| WO | 2017/100402 | | 6/2017 | |
| WO | WO-2020116411 | A1 * | 6/2020 | A61K 8/361 |
| WO | 2021/122972 | | 6/2021 | |
| WO | 2021/122973 | | 6/2021 | |
| WO | 2022/175141 | | 8/2022 | |
| WO | 2022/263149 | | 12/2022 | |

OTHER PUBLICATIONS

Cui et al., “Insights Into the Synthesis of Isosorbide Diester Plasticizer using Immobilized Lipases” RSC Advances, vol. 6, Nov. 7, 2016, pp. 108180-108186.

Giacometti et al., “Process for Preparing Nonionic Surfactant Sorbitan Fatty Acid Esters with and without Previous Sorbitol Cyclization”, Journal of Agriculture and Food Chemistry, vol. 44, No. 12, 1996, pp. 3950-3954.

International Search Report received for PCT Application No. PCT/EP2022/064532, mailed on Sep. 20, 2022, 6 pages.

Joseph F. Treon, “Physiological Properties of Selected Non-Ionic Surfactants”, Jan. 1965, pp. 47-54.

Kurszewska et al., “Solvent-Free Thermal Dehydration of Pentitols on Zeolites”, Journal of Carbohydrate Chemistry, vol. 23, No. 4, 2004, pp. 169-177.

Pruvost et al., “Synthesis of 1, 4:3, 6-Dianhydrohexitols Diesters from the Palladium-Catalyzed Hydroesterification Reaction” ChemSusChem, 2014, DOI:10.1002/cssc.201402584, 8 pages.

Rose et al., “Isosorbide as a Renewable Platform chemical for Versatile Applications—Quo Vadis?”, ChemSusChem, vol. 5, 2012, pp. 167-176.

Soutelo-Maria et al., “Oxidative Cleavage of Fatty Acid Derivatives for Monomer Synthesis”, Catalysts, vol. 8, No. 464, 2018, pp. 1-17.

Written Opinion received for PCT Application No. PCT/EP2022/064532, mailed on Sep. 20, 2022, 9 pages.

U.S. Appl. No. 17/757,576, filed Jun. 17, 2022, 2023/0055814, Von Hof et al.

U.S. Appl. No. 11/491,093, filed Nov. 8, 2022, 2020/0375862, Brandt et al.

U.S. Appl. No. 17/757,711, filed Jun. 17, 2022, 2023/0033620, Liebig et al.

U.S. Appl. No. 11/757,528, filed Jun. 16, 2022, 2023/0023141, Von Hof et al.

Office Action received for U.S. Appl. No. 18/570,018, mailed on Feb. 5, 2026, 17 pages.

U.S. Appl. No. 18/570,018, filed Dec. 13, 2023, 2024/0270676, Liebig et al.

* cited by examiner

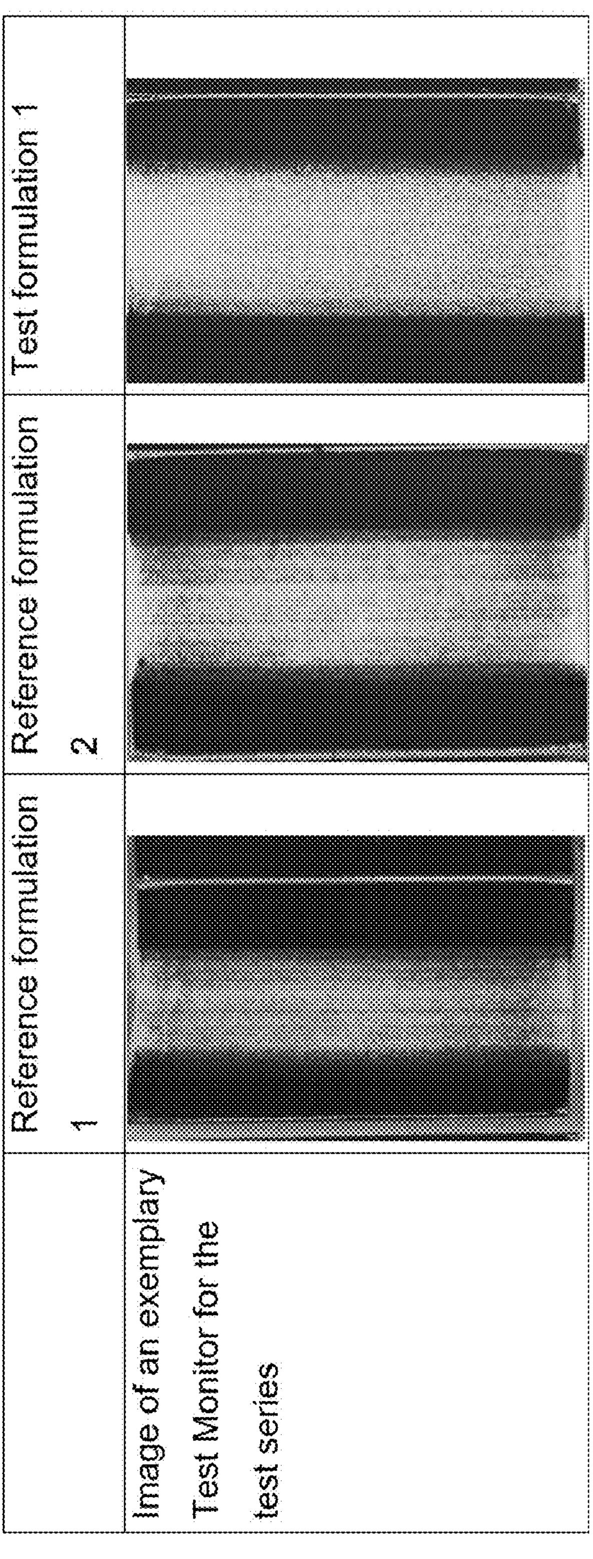
Test formulation 1
Reference formulation 2
Reference formulation 1
Image of an exemplary Test Monitor for the test series

COMPOSITIONS COMPRISING N-NONANOIC ACID ESTERS OF XYLITAN AND/OR SORBITAN

CROSS-REFERENCE TO RELATED APPLICATIONS

This application is a National Stage entry under § 371 of International Application No. PCT/EP2022/064532, filed on May 30, 2022, and which claims the benefit of priority to European Patent Application No. 21180241.8, filed on Jun. 18, 2021. The content of each of these applications is hereby incorporated by reference in its entirety.

BACKGROUND OF THE INVENTION

Field of the Invention

The invention relates to compositions comprising n-nonanoic acid esters of xylitan and/or sorbitan, a method for their production, formulations comprising them and their use.

Description of Related Art

EP2410979 discloses formulations for the cleansing and care of human or animal body parts containing sorbitan carboxylic acid esters, characterized in that the carboxylic acid component of the sorbitan carboxylic acid ester is derived from a carboxylic acid containing 6 to 10 carbon atoms and the sorbitan carboxylic acid esters have a hydroxyl number (OH number) of greater than 350.

EP3744310 discloses compositions comprising

A) at least one sorbitan carboxylic ester of at least one carboxylic acid selected from carboxylic acids having 6 to 12 carbon atoms, wherein all sorbitan carboxylic esters present in component A together have on average a degree of esterification of 0.7 to 2.1 carboxylic acid radicals per sorbitan carboxylic ester, B) at least one glycerol carboxylic ester of at least one carboxylic acid selected from carboxylic acids having 6 to 22 carbon atoms, wherein all glycerol carboxylic esters present in component B together have on average a degree of esterification of 0.7 to 1.5 carboxylic acid radicals per glycerol carboxylic ester, and C) water, characterized in that components A) and B) in sum total are present to an extent of at least 50% by weight based on the total composition.

KR101939851B1 describes esters of dehydrated xylitol and the use of these carboxylic esters of anhydroxylitol as rheological additive/viscosity regulator in an emulsion.

Dishes and cutlery, that is repeatedly cleaned in a dishwasher often suffer from deposits of the rinse aid and/or the detergent used. These quite frequently leads to a bitter taste when food is consumed from these dishes or cutlery. The same is true for glasses and beverages.

It is an object of the invention to reduce deposits arising in dishwashing.

SUMMARY OF THE INVENTION

It was found that, surprisingly, n-nonanoic acid esters of xylitan and/or sorbitan solve this problem.

The present invention therefore provides anhydro sugar alcohol n-nonanoic acid ester composition comprising the anhydro sugar alcohol and different anhydro sugar alcohol mono n-nonanoic esters, wherein the anhydro sugar alcohol is selected from sorbitan and xylitan, preferably sorbitan.

The invention further provides a method for production of and formulations comprising the anhydro sugar alcohol n-nonanoic acid ester compositions according to the instant invention, as well as the use of anhydro sugar alcohol n-nonanoic acid ester compositions according to the instant invention to prevent and/or reduce deposits on dishes, glasses and cutlery from dishwashing processes.

One advantage of the compositions of the instant invention is their improved odor profile.

Another advantage of the present invention is that—although sorbitan esters are known as foaming enhancers—the compositions of the instant invention do not induce high foaming in automatic dish washing processes.

A further advantage is that the compositions of the instant invention are cleaning boosters for the cleaning industry with exceptional good wetting properties Another advantage of the present invention is that the compositions of the instant invention bear a fast dirt penetration.

A further advantage is that the compositions of the instant invention have excellent cleaning power, especially on soil removal even on very difficult and hard to remove soils.

Another advantage of the present invention is that that the compositions of the instant invention have high dispersing and emulsifying properties.

A further advantage is that the compositions of the instant invention hinder soil redeposition efficiently.

Another advantage of the present invention is that that the compositions of the instant invention support the sheeting effect during the rinsing step, which leads to a fast and residue free drying surfaces.

Another advantage is that the composition of the instant invention exhibits superior properties in terms of unwanted remnants of fragrance and/or odor as well taste on rinsed dishes.

Another advantage of the present invention is that the compositions of the instant invention are readily biodegradable.

Another advantage of the present invention is that the compositions of the instant invention show effective make-up removal properties.

Another advantage of the present invention is that the compositions of the instant invention provide effective solubilizing properties for emollients and fragrances.

Another advantage of the present invention is that the compositions of the instant invention provide effective thickening properties in aqueous cosmetic cleansing formulations.

Another advantage of the present invention is that the compositions of the instant invention show effective co-emulsifying properties in cosmetic creams and lotions.

Another advantage of the present invention is that the compositions of the instant invention provide effective moisturizing properties in cosmetic formulations.

Another advantage of the present invention is that the compositions of the instant invention do not need to be preserved due to the absence or low content of water.

Another advantage of the present invention is that the compositions of the instant invention have a long shelf life of >12 months due to the absence or low content of water and the resulting avoidance of hydrolysis.

Another advantage of the present invention is that the compositions of the instant invention do not contain any petrochemical based polyethylene glycol.

Another advantage of the present invention is that the compositions of the instant invention are cold-processable, which results in less energy consumption during processing.

Another advantage of the present invention is that the compositions of the instant invention can be obtained from palm-free raw materials, which helps to reduce the climate change due to a reduction of the deforestation of the rain forest.

BRIEF DESCRIPTION OF THE DRAWINGS

The FIGURE shows the cleaning performance results.

DETAILED DESCRIPTION OF THE INVENTION

Presently described thus are anhydro sugar alcohol n-nonanoic acid ester composition comprising, A) anhydro sugar alcohol, B) anhydro sugar alcohol mono n-nonanoic ester, and C) anhydro sugar alcohol di n-nonanoic ester, wherein the anhydro sugar alcohol is selected from sorbitan and xylitan, preferably sorbitan.

Nonanoic Acid/Pelargonic Acid n-Nonanoic acid (pelargonic acid, CAS 112-05-0) can be obtained by oxidation of n-nonanal of petrochemical origin ("*Carboxylic Acids, Aliphatic*," in: *Ullmann's Encyclopedia of Industrial Chemistry* 2014). Alternatively, n-nonanoic acid can be obtained by ozonolysis of ω-9-fatty acids, for example oleic acid and erucic acid, or esters thereof. However, ozonolysis is a process having high energy demand and specific process requirements, for example the use of an ozone generator. Moreover, the ω-9-fatty acids used have often been obtained from tropical oils, for example palm oil, palm kernel oil and coconut oil. Much more sustainable processes for preparing n-nonanoic acid are based on hydrogen peroxide (Soutelo-Maria et al. in *Catalysts* 2018, 8, 464), particularly processes as, for example, in U.S. Pat. Nos. 9,272,975, 8,846,962, 8,222,438, WO2007039481 and WO2011080296, if they are also conducted proceeding from ω-9-fatty acids or esters thereof that have not been obtained from tropical oils.

Sorbitan

Sorbitan is in general understood as meaning a product mixture of the self-condensation products of sorbitol, mainly 1,4-anhydro-sorbitol, 2,5-anhydro-sorbitol, 1,5-anhydro-sorbitol (Advances in Carbohydrate Chemistry and Biochemistry, 1983, 41, 27-66) and isosorbide (1,4:3,6-Dianhydro-Sorbitol; ChemSusChem. 5 (1): 167-176); these are essentially five- and six-membered, mono- and bicyclic, hydroxyl-functional ethers of polyol character, as shown exemplarily by the following formulae:

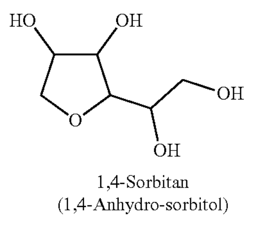

1,4-Sorbitan
(1,4-Anhydro-sorbitol)

-continued

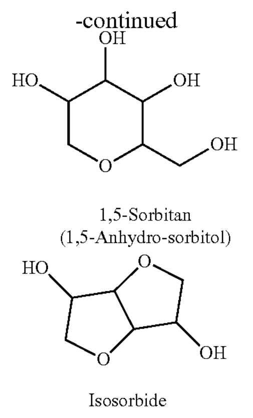

1,5-Sorbitan
(1,5-Anhydro-sorbitol)

Isosorbide

In such mixtures, further condensation products and also sorbitol are in general contained to a minor extent.

Sorbitan esters are the esters of sorbitan and thus the esterification products of the polyol mixture described above with organic acids.

A summary presentation of sorbitan esters is found, for example, in Treon, Soap Perfumery Cosmetics, January 1965, p. 47.

Xylitan

Xylitan is in general understood as meaning a product mixture of the self-condensation products of xylitol.

Three main condensation products of xylitol that are comprised in xylitan are the anhydropentitols 1,4-anhydroxylitol, 1,4-anhydroarabinitol and 1,4-anhydroribitol (*J. Carbohydr. Chem.* 2004, 23, 4, 169-177 and *Adv. Carbohydr. Chem. Biochem.,* 1983, 41, 27-66). As described above for sorbitan, a person skilled in the art understands, that xylitan also may contain uncondensed xylitol to a minor extend.

Xylitan esters are the esters of xylitan and thus the esterification products of this above-described polyol mixture with organic acids.

Unless stated otherwise, all percentages (%) given are percentages by mass.

Preferred anhydro sugar alcohol n-nonanoic acid ester compositions according to the instant invention are characterized in that they further comprise D) anhydro sugar alcohol tri n-nonanoic ester, and/or, preferably and E) anhydro sugar alcohol tetra n-nonanoic ester.

As described above sorbitan and xylitan may contain some sorbitol or xylitol respectively; thus, the sugar alcohol n-nonanoic acid ester compositions of the instant invention, of course, will preferably contain some sorbitol n-nonanoic esters and/or xylitol n-nonanoic esters, respectively.

If sorbitol n-nonanoic esters and/or xylitol n-nonanoic esters are contained in the sugar alcohol n-nonanoic acid ester compositions of the instant invention, all parameters described below will regard their content.

It is preferred, if the anhydro sugar alcohol n-nonanoic acid ester composition according to the instant invention comprises F) free n-nonanoic acid.

The free n-nonanoic acid may be in protonated or neutralized form.

The content of free n-nonanoic acid in the anhydro sugar alcohol n-nonanoic acid ester composition according to the instant invention is determined by first determining the acid number.

This can be used to determine the proportion by weight of n-nonanoic acid via the molar mass thereof.

Suitable methods for determining the acid number are especially those according to DGF C-V 2, DIN EN ISO 2114, Ph.Eur. 2.5.1, ISO 3682 and ASTM D 974.

The saponification value is determined by those skilled in the art in accordance with DGF C-V 3 or DIN EN ISO 3681.

Suitable methods for determining the hydroxyl value are especially those according to DGF C-V 17 a (53), Ph.Eur. 2.5.3 Method A and DIN 53240.

A preferred anhydro sugar alcohol n-nonanoic acid ester composition of the instant invention is characterized in that the anhydro sugar alcohol n-nonanoic acid ester has an average degree of esterification of 0.7 to 4.0, preferably 0.8 to 2.5, particularly preferably 1.0 to 2.0.

A preferred anhydro sugar alcohol n-nonanoic acid ester composition of the instant invention is characterized in that the anhydro sugar alcohol n-nonanoic acid ester has a saponification value of 100 to 350, preferably 125 to 300, particularly preferably 150 to 275 mg, KOH/g.

A preferred anhydro sugar alcohol n-nonanoic acid ester composition of the instant invention is characterized in that the anhydro sugar alcohol n-nonanoic acid ester has an acid value of 0.1 to 40, preferably 0.5 to 30, particularly preferably 1 to 20 mg, KOH/g.

A preferred anhydro sugar alcohol n-nonanoic acid ester composition of the instant invention is characterized in that the anhydro sugar alcohol n-nonanoic acid ester has a hydroxyl number (OH number) of 50 to 600, preferably 100 to 550, particularly preferably 150 to 500 mg, KOH/g.

A preferred anhydro sugar alcohol n-nonanoic acid ester composition of the instant invention is characterized in that the weight ratio of anhydro sugar alcohols to their corresponding sugar alcohols (sorbitol/xylitol) in the anhydro sugar alcohol n-nonanoic acid ester composition of the instant invention is preferably greater than 60 to 40, preferably greater than 70 to 30, more preferably greater than 80 to 20 in particular preferably greater than 85 to 15 as determined by HPLC analysis. A detailed description of suitable analytical methods can be found in WO2021122972 for xylitol esters containing xylitan esters and WO2021122973 for sorbitol esters containing sorbitan esters.

A further subject of the instant invention is a method for the production of an anhydro sugar alcohol n-nonanoic acid ester composition, wherein the anhydro sugar alcohol is selected from sorbitan and xylitan, preferably of one according to the instant invention, comprising the steps of, I) providing sorbitol and/or xylitol, preferably sorbitol, II) dehydrating at least parts of the sorbitol and/or xylitol to sorbitan and/or xylitan, preferably sorbitan, III) esterification of the sorbitan and/or xylitan, preferably sorbitan, with n-nonanoic acid, and optionally IV) isolation of formed anhydro sugar alcohol n-nonanoic acid ester composition from process step III).

In process step II) of the method according to the instant invention, the sorbitol and/or xylitol is dehydrated to give a mixture of various isomers, for instance 1,4-anhydro-sorbitol, 2,5-anhydro-sorbitol, 1,5-anhydro-sorbitol, isosorbide and if so residual sorbitol.

Preferably at least 60 wt.-%, more preferably at least 70 wt.-%, even more preferably at least 80 wt.-%, most preferably at least 85 wt.-%, of the sorbitol and/or xylitol provided are dehydrated in process step II) of the method according to the instant invention.

The reaction conditions in process step II) have an influence on the composition of the dehydration product.

Process step II) of the method according to the instant invention is preferably carried out at a temperature between 100° C. and 300° C., preferably between 120° C. and 240° C., in particular between 130° C. and 200° C.

In addition process step II) of the method according to the instant invention is preferably carried out at a pressure between 0.001 bar and 1.5 bar, preferably between 0.5 bar and 1.25 bar, in particular between 0.8 bar and 1.2 bar.

In a preferred, alternative embodiment preparation process step II) of the method according to the instant invention is carried out at a pressure between 0.001 bar and 0.9 bar, preferably between 0.005 bar and 0.5 bar, in particular between 0.006 bar and 0.01 bar and at a temperature between 80° C. and 140° C., preferably between 90° C. and 130° C., in particular between 95° C. and 120° C. The use of an acid catalyst, as described for example in EP 0280780, can have an influence on the dehydration product. Process step II) of the method according to the instant invention is preferably carried out with an acid catalyst, preferably phosphoric acid.

Process step III) of the method according to the instant invention can be conducted via classical chemical routes or via enzymatic routes.

A quick and if possible quantitative reaction in process step III) of the method according to the instant invention via classical chemical routes is dependent on the various parameters such as pressure, temperature and qualitative ratio of the reaction partners to one another. These parameters likewise influence the anhydro sugar alcohol n-nonanoic acid ester composition with respect to statistical distribution, for example of various isomers, produced by, for example, different possibilities of the esterification position in the molecule, which can lead to different mixtures of mono-, di- and tri-esters.

A preferred method according to the invention is characterized in that process step III) of the method according to the instant invention is carried out at a temperature between 140° C. and 300° C., preferably between 160° C. and 250° C., in particular between 200° C. and 230° C.

Analogously, it is preferable that process step III) is carried out at a pressure between 0.001 bar and 1.5 bar, preferably between 0.5 bar and 1.25 bar, in particular between 0.8 bar and 1.2 bar.

In a preferred, alternative embodiment of the method according to the invention process step III) is carried out at a pressure between 0.001 bar and 0.9 bar, preferably between 0.05 bar and 0.5 bar, in particular between 0.006 bar and 0.01 bar and at a temperature between 80° C. and 250° C., preferably between 120° C. and 220° C., in particular between 150° C. and 200° C.

Just as in process step II) of the method according to the instant invention, the use of a catalyst in process step III) of the method according to the instant invention, such as alkali metal hydroxides, alkali metal carbonates or alkali metal salts of phosphoric acid, phosphorous acid or hypophosphorous acid can have an influence on the anhydro sugar alcohol n-nonanoic acid ester composition.

Preferably in process step III) of the method according to the instant invention at least one catalyst selected from the group comprising alkali metal salts and alkaline earth metal salts, preferably sodium hydroxide, is employed.

For process step III) of the method according to the instant invention) to be carried out via enzymatic routes, the methods of EP3839052 can be applied.

It is obvious, that sorbitol and/or xylitol present in process step III) of the method according to the instant invention is also esterified with the n-nonanoic acid.

Preferably, process step II) and process step III) are carried out in a one-pot process. This means, that at least part of the catalyst used for esterification is already present during the dehydration. Thus, sorbitol and/or xylitol, preferably sorbitol, n-nonanoic acid and the catalyst are provided and the mixture is heated to a temperature between 100° C. and 300° C., preferably between 120° C. and 275° C., more preferably between 140° C. and 250° C., even more preferably between 180° C. and 240° C., in particular between 200° C. and 230° C. while applying a pressure between 0.01 bar and 1.5 bar, preferably between 0.1 bar and 1.25 bar, in particular between 0.8 bar and 1.2 bar.

Optionally, process step II) and/or process step III) or the one-pot process described above can be carried out in the presence of activated carbon.

This has the effect, that the anhydro sugar alcohol n-nonanoic acid ester composition produced by the method of the instant invention has an improved color profile.

Optionally, the obtained n-nonanoic acid esters of xylitan and/or sorbitan can be treated with aqueous solutions of hydrogen peroxide, preferably by applying a net/active amount of hydrogen peroxide of 0.01 to 1.0%, preferably 0.05 to 0.5%, for 5 to 500 min at 60 to 140° C.

A further subject of the instant invention is a formulation comprising an anhydro sugar alcohol n-nonanoic acid ester composition according to the instant invention or obtainable by the method of the instant invention, characterized in that the formulation comprises from 0.01% by weight to 10% by weight of the anhydro sugar alcohol n-nonanoic acid ester composition based on the total formulation.

The formulation according to the instant invention preferably is a cosmetic or household care formulation, preferably for cleaning. Preferred formulations are dish washing formulations and laundry detergents.

Therefore, preferably the formulations according to the instant invention preferably comprise at least one surfactant.

The anhydro sugar alcohol n-nonanoic acid ester composition according to the invention may have surfactant properties; in the context of the present invention these anhydro sugar alcohol n-nonanoic acid ester compositions are not counted as surfactants.

Surfactants comprised in the formulation according to the instant invention may be, for example, anionic, non-ionic or amphoteric surfactants.

Typical examples of anionic surfactants are fatty alcohol sulfates, fatty alcohol polyglycol ether sulfates, monoglyceride sulfates, mono- and/or dialkyl sulfosuccinates, fatty acid isethionates, fatty acid sarcosinates, fatty acid taurates, fatty acid glutamates, fatty acid glycinates, alkyl ether carboxylates.

Non-ionic surfactants are, for example, alkyl oligoglucosides, fatty acid glucamides, rhamnolipids, sophorolipids and/or protein fatty acid condensates, the latter for example based on wheat proteins.

Amphoteric surfactants are, for example, alkylamidoalkyl hydroxysultaines, alkylamidoalkyl betaines, alkyl betaines, amphoacetates and amphopropionates, the terminal acyl or alkyl radicals of which typically comprise 8 to 18 carbon atoms.

Surfactants particularly included in accordance with the invention are fatty alcohol sulfates, fatty alcohol polyglycol ether sulfates, mono- and/or dialkyl sulfosuccinates, amphoacetates, amphopropionates, alkyl betaines, cocamidopropyl betaines, alkyl oligoglucosides and fatty acid glutamates.

Surfactants particularly preferably included in accordance with the invention are the polyether-free surfactants mono- and/or dialkyl sulfosuccinates, amphoacetates, amphopropionates, betaines, especially cocamidopropyl betaines, alkyl oligoglucosides and fatty acid glutamates.

In accordance with the invention, the preferred amount of surfactant included is used such that the resulting formulation comprises at least 2% by weight, preferably at least 4% by weight and particularly preferably at least 6% by weight total surfactant, based on the total formulation.

A preferred formulation according to the instant invention is characterized in that it has a pH of 2 to 13, preferably 4 to 12.

The “pH” in connection with the present invention is defined as the value which is measured for the relevant composition at 25° C. after stirring for five minutes using a pH electrode calibrated in accordance with ISO 4319 (1977).

In case the formulations are to be used as rinse aids and/or bathroom cleaners, then it is preferred that the formulations according to the instant invention are characterized in that they have a pH of 2.5 to 6.5, preferably 3.0 to 5.4.

In case the formulations are to be used as hand dish wash cleaners, then it is preferred that the formulations according to the instant invention are characterized in that they have a pH of 4.0 to 7.0, preferably 5.0 to 6.0.

In case the formulations are to be used as automatic dish wash cleaners, all-purpose cleaners, hard surface cleaners, floor cleaners, metal cleaners, car shampoos, kitchen cleaners, laundry detergents, glass cleaners, food and beverage cleaners then it is preferred that the formulations according to the instant invention are characterized in that they have a pH of 7.0 to 14.0, preferably 7.5 to 12.5.

A further subject of the instant invention is the use of an anhydro sugar alcohol n-nonanoic acid ester composition according to the instant invention, obtainable by the method of according to the instant invention or a formulation according to according to the instant invention to prevent and/or reduce deposits on dishes, glasses and cutlery from dishwashing processes.

The examples adduced hereinafter describe the present invention by way of example, without any intention that the invention, the scope of application of which is apparent from the entirety of the description and as described herein, be restricted to the embodiments specified in the examples.

EXAMPLES

Examples 1a to 1f: Synthesis of n-Nonanoic Acid Esters of Xylitan or Sorbitan (Inventive)

Xylitol or sorbitol (or aqueous solutions thereof) were initially charged together with n-nonanoic acid and, after the catalyst had been added, the reaction mixture was heated to reaction temperature while stirring at the pressure specified within 1 h, and the water formed was removed continuously until the acid number specified had been attained. Finally, the mixture was filtered through a filter press.

TABLE 1

| | Sugar alcohol | Sugar alcohol m [g] | Sugar alcohol n [mol] | Pelargonic acid m/g | Pelargonic acid n [mol] | Pelargonic acid Equiv. | Catalyst | Reaction conditions | Acid number of the product [mg KOH/g] |
|---|---|---|---|---|---|---|---|---|---|
| 1a | Xylitol | 290.1 | 1.91 | 467.6 | 2.96 | 1.55 | 3.7 g $H_3PO_4$ and 6.6 g NaOH | 230° C., 1 atm | 7.9 |
| 1b | Xylitol | 290.0 | 1.91 | 392.1 | 2.48 | 1.30 | 0.8 g para-toluenesulfonic acid | 160° C., 1 atm | 5.7 |
| 1c | Xylitol | 275.0 | 1.81 | 486.2 | 3.07 | 1.70 | 19.4 g $K_2CO_3$ | 180° C., 50 mbar | 7.1 |
| 1d | Sorbitol (70% aqueous solution) | 390.5 | 1.50 | 368.0 | 2.33 | 1.55 | 2.9 g $H_3PO_4$ and 5.0 g NaOH | 230° C., 1 atm | 8.6 |
| 1e | Sorbitol (70% aqueous solution) | 389.7 | 1.50 | 308.0 | 1.95 | 1.30 | 0.6 g para-toluenesulfonic acid | 160° C., 1 atm | 5.6 |
| 1f | Sorbitol (70% aqueous solution) | 370.2 | 1.42 | 382.6 | 2.42 | 1.70 | 15.3 g $K_2CO_3$ | 180° C., 50 mbar | 6.9 |

Example 1g: Synthesis of a n-Octanoic/n-Decanoic Acid Ester of Sorbitan (Non-Inventive)

This product was synthesized as an analogue of example 1d by only exchanging the pelargonic acid by a 75:25 (w/w) mixture of caprylic acid and capric acid. The acid number of the product was analyzed to be 13.4 mg KOH/g.

Example 2: Odor Panel

The products of the examples 1d and 1g were compared in an odor panel test according to the state of the art. A group consisting of 7 experienced testers, which were qualified by a triangle test procedure before, smelled at 30 ml of both products, which were previously stored for 12 hours in a closed 100 ml brown wide neck glass bottle. The odor was evaluated by the 7 testers based on a rating scale from 1 (good) over 2 (acceptable) to 3 (poor).

As a result of this test, the product of example 1d received an average panel rating of 1.43 and the product of example 1g received an average panel rating of 2.14.

Example 3

This example demonstrates the cleaning enhancing effect of composition from Example 1f compared to composition described in example 1g when used in formulations of household cleaners.

Exemplary formulations described in the table 1 have been prepared according to the following protocol. Initially, a measured amount of water was introduced into a glass beaker of a suitable size. Subsequently, further constituents were added at room temperature and under vigorous stirring. The ingredients were added in no specific or uniform sequence as the order of addition to the solution was not critical. Finally, any remaining amount of water was introduced to ensure desired concentration of ingredients. All ingredients were mixed using a magnetic stirrer and pH of the solution was adjusted to 8.0 by addition of citric acid. The mixture was then stirred for 5 minutes to ensure a homogenous solution. The exemplary compositions were easily pourable and stable at room temperature for extended period.

According to the above-described method, three formulations were prepared (table 1):

Reference formulation 1, that was subsequently used as a control formulation to evaluate effect of tested cleaning boosting additives Reference formulation 2, that contained ingredients of the Reference formulation 1 and a benchmark cleaning booster, composition described in example 1g, Test formulation 1, that contained ingredients of the Reference formulation 1 and the object of the invention, composition from Example 1f Table 1: Compositions of test formulation 1 and reference formulations evaluated in cleaning performance tests.

TABLE 1

Compositions of test formulation 1 and reference formulations evaluated in cleaning performance tests.

| | Reference formulation 1/% | Reference formulation 2/% | Test formulation 1/% |
|---|---|---|---|
| Composition from example 1g | | 0.75 | |
| Composition from example 1f | | | 0.75 |
| Rewoferm RL 100 | 5.00 | 5.00 | 5.00 |
| Sodium carbonate | 1.00 | 1.00 | 1.00 |
| Sodium Citrate | 3.00 | 3.00 | 3.00 |
| Phenoxyethanol | 0.20 | 0.20 | 0.20 |
| Citric acid | to achieve pH 8.0 | to achieve pH 8.0 | to achieve pH 8.0 |
| Water | to 100 | to 100 | to 100 |

Subsequently, cleaning performance of Test formulation 1 was evaluated against two reference formulations described in table 1. The procedure used for the evaluating the cleaning performance is described in the following test protocol.

Cleaning performance test was conducted according to the internal test methodology, which was adapted from the recommendation of German Cosmetic, Toiletry, Perfumery and Detergent Association (IKW): "IKW Recommendation for the Quality Assessment of the Product Performance of All-Purpose Cleaners 2014" (IKW Test Protocol). The principle of the test was to evaluate the cleaning power of tested formulations by assessing their efficacy in removal of stubborn soil deposited on melamine tiles. White, melamine tiles covered with black, stubborn soil composed of mixture of fat and carbon black (here called Test Monitors) were purchased from Center for Test materials B.V. (available under the name DM-40 Tile). To ensure high reproducibility of the results, all Test Monitors belonged to the same production batch and were conditioned prior to use for 24 hours at 20° C. inside a climatic chamber.

To evaluate cleaning performance of the prepared formulations, Test Monitors were placed in a TQC Sheen washability tester (model AB5000) and locked in a position. One Test Monitor was placed in the Washability Tester at the time, but it was ensured that for each of the cleaning formulations, the test was conducted at least once at each of the four tracks of the Washability Tester. Subsequently, dry, 9 cm by 4.5 cm sponges were first moistened with tap water, and water excess was wrung out from sponges. Thereafter, 10 g of the test solution was loaded onto the sponge and sponge was attached to the cleaning arm of the Washability Tester. Washability Tester was then actuated and controlled to provide 10 cleaning cycles (so 20 linear strokes) over the Test Monitor. The speed of the strokes for 20 cycles per minute and the test was performed at room temperature. After 10 cleaning cycles were completed, the Test Monitor was removed from the Sheen tester, rinsed with tap water, and allowed to dry. The test was repeated several times to provide 5 replicates for each tested composition.

The treated Test Monitors were visually evaluated by five panelists who were asked to rate the cleaning efficacy achieved by each of the compositions. Panellists ranked the cleaning efficacy on a scale from 0 to 10, with 0 representing no observed cleaning and 10 representing a complete removal of the stain. For comparative purposes, each of the panelists was provided with a new, soiled Test Monitor that represented no cleaning as well as with a fully cleaned Test Monitor that represented the score of 10. Additionally, the panelists were provided with the evaluation template according to IKW Test Protocol to enable more accurate assessment of cleanness. The scores were summed and averaged for each of the tested composition and the results are reported in table 2.

TABLE 2

Cleaning performance results for tested compositions (average cleaning score, 0 - no cleaning, 10 - complete cleaning, and photographs of exemplary Test Monitors).

| | Reference formulation 1 | Reference formulation 2 | Test formulation 1 |
|---|---|---|---|
| Average cleaning score | 4.60 | 5.84 | 7.40 |

As is readily evident from the results reported in the table 2, the composition containing object of invention delivers superior cleaning performance results to both benchmarks. Test formulation 1 by far exceeds cleaning results achieved by Reference formulation 1 that does not contain any cleaning booster as well as it delivers much better cleaning than Reference formulation 2, so composition containing the benchmark cleaning booster.

FIG. 1 clearly shows the visible result.

Example 4

This example demonstrates superior properties of composition from Example 1f when compared to benchmark surfactants such as fatty alcohol ethoxylates in terms of fragrance remaining on rinsed dishes.

The panel test was performed according to the following protocol:

Initially, two test solutions were prepared. Benchmark Solution contained 0.5 wt. %. of an exemplary fatty alcohol ethoxylate in tap water. Test Solution contained 0.5 wt. %. of composition from Example 1f in tap water. Thereafter, two sets of clean, ceramic plates were used to perform tests. Plates from the first set were immersed in Benchmark Solution and the plates from the second set in Test Solution. Subsequently, plates were allowed to drain and were subjected to a blind test evaluation by a team of 5 panelists. Each of the panelists received two plates, one that had previously been immersed in Benchmark Solution and the second that had been immersed in Test Solution. The panelists were asked to assess the smell of both plates and describe them according to the following methodology:

Smell of the plates was assessed on the scale from −1 to +1, with −1 meaning unpleasant, 0—neutral, +1—pleasant Panellists were also allowed to share additional comments regarding the recognized smell.

As the result, 4 out of 5 panelists described the smell of the plates immersed in Benchmark Solution as unpleasant and a further 1 panelist described it as neutral. Moreover, 3 panelists described the smell of the plates immersed in the Test Solution as pleasant and further 2 panelists described it as neutral. In addition, the smell of plates previously immersed in composition from example 1f solution was described as "reminding the smell of the coconut" by 3 of the panelists, and 4 panelists described the smell of the plates immersed in Benchmark Solution as either "artificial" or "chemical". Such a scent can be considered a common characteristic of fatty alcohol ethoxylate surfactants.

| | Benchmark Solution | Composition from example 1f solution |
|---|---|---|
| Panel Person 1 | −1 | 1 |
| Panel Person 2 | 0 | 1 |
| Panel Person 3 | −1 | 0 |
| Panel Person 4 | −1 | 0 |
| Panel Person 5 | −1 | 1 |

Moreover, the same test was repeated using this time spoons made from stainless steel. Thereafter, two sets of clean, spoons were used to perform tests. Spoons from the first set were immersed in Benchmark Solution and the spoons from the second set in Composition from Example 1f Solution. Subsequently, the spoons were allowed to drain and were subjected to a blind test evaluation by a team of 5 panelists. Each of the panelists received two spoons, one that had previously been immersed in Benchmark Solution and the second that had been immersed in Composition from Example 1f Solution. The panelists were asked to assess the taste of both spoons and describe them according to the following methodology:

Taste of the spoons s was assessed on the scale from −1 to +1, with −1 meaning unpleasant, 0—neutral, +1—pleasant As the result, 3 out of 5 panelists described the taste of the spoons immersed in Benchmark Solution as neutral and a further 2 panelists described it as unpleasant. Moreover, 3 panelists described the taste of the spoons immersed in the Test Solution as neutral and further 2 panelists described it as pleasant.

| | Benchmark Solution | Composition from example 1f solution |
|---|---|---|
| Panel Person 1 | 0 | 1 |
| Panel Person 2 | 0 | 1 |
| Panel Person 3 | −1 | 0 |
| Panel Person 4 | 0 | 0 |
| Panel Person 5 | −1 | 0 |

As evident from the presented example, the object of the invention allows to formulate products with purpose of cleaning or rinsing dishes without the risk of leaving unpleasant scent on the dishes. Instead, the dishes may have a slight scent of coconut that is assessed as pleasant by most panelists.

Example Formulations

| Recipes 1a, 1b, 1c and 1d: Shower cream | | | | |
|---|---|---|---|---|
| | 1a | 1b | 1c | 1d |
| Water | to 100.0% | to 100.0% | to 100.0% | to 100.0% |
| Composition from Example 1a | 1.5% | | | |
| Composition from Example 1c | | 1.5% | | |
| Composition from Example 1d | | | 1.5% | |
| Composition from Example 1f | | | | 1.5% |
| Sodium Laureth Sulfate (Texapon NSO. BASF. 28%) | 25.0% | 25.0% | 25.0% | 25.0% |
| Coco-Glucoside (Plantacare 818 UP. BASF. 51%) | 8.0% | 8.0% | 8.0% | 8.0% |
| Cocamidopropyl Betaine (TEGO ® Betain F 50. Evonik. 38%) | 8.0% | 8.0% | 8.0% | 8.0% |
| PEG-18 Glyceryl Oleate/Cocoate (ANTIL ® 171. Evonik) | 1.5% | 1.5% | 1.5% | 1.5% |
| Sorbitan Sesquicaprylate (ANTIL ® Soft SC. Evonik) | 0.8% | 0.8% | 0.8% | 0.8% |
| Glyceryl Oleate (TEGIN ® O V. Evonik) | 0.8% | 0.8% | 0.8% | 0.8% |
| Perfume Spicy Herbs (IFF) | 0.2% | 0.2% | 0.2% | 0.2% |
| Polyglyceryl-4 Caprate (TEGOSOFT ® PC 41. Evonik) | 0.6% | 0.6% | 0.6% | 0.6% |
| *Helianthus Annuus* Seed Oil (AEC Sunflower Oil. A & E Connock. Perfumery & Cosmetics Ltd.) | 0.2% | 0.2% | 0.2% | 0.2% |
| Linalool (Lipofresh. Lipo Chemicals. Inc.) | 0.1% | 0.1% | 0.1% | 0.1% |
| Coumarin (Rhodiascent extra pure. Solvay Rhodia) | 0.1% | 0.1% | 0.1% | 0.1% |
| Glycerol (Glycerol EP. vegetable. Spiga Nord) | 0.4% | 0.4% | 0.4% | 0.4% |
| Hydroxypropyl Methylcellulose (TEGOCEL ® HPM 50. Evonik) | 0.2% | 0.2% | 0.2% | 0.2% |
| Glycol Distearate (TEGIN ® G 1100 Pellets. Evonik) | 0.4% | 0.4% | 0.4% | 0.4% |
| Sodium Chloride | 0.5% | 0.5% | 0.5% | 0.5% |
| Hydroxypropyl Guar Hydroxypropyltrimonium Chloride (Jaguar C-162. Solvay Rhodia) | 0.2% | 0.2% | 0.2% | 0.2% |
| dermofeel TOCO 70 non GMO | 0.1% | 0.1% | 0.1% | 0.1% |
| Disodium EDTA (Dissolvine NA-2-P. AkzoNobel) | 0.1% | 0.1% | 0.1% | 0.1% |
| Preservative | q.s. | q.s. | q.s. | q.s. |
| Citric Acid | to pH 5.2 | to pH 5.2 | to pH 5.2 | to pH 5.2 |

| Recipes 2a, 2b, 2c and 2d: Body shampoo | | | | | |
|---|---|---|---|---|---|
| | | 2a | 2b | 2c | 2d |
| Phase A | Composition from Example 1a | 0.5% | | | |
| | Composition from Example 1c | | 0.5% | | |
| | Composition from Example 1d | | | 0.5% | |
| | Composition from Example 1f | | | | 0.5% |
| | *Lavandula Angustifolia* (Lavender) Oil (AEC Lavender Oil. A&E Connock Ltd.) | 0.2% | 0.2% | 0.2% | 0.2% |
| | Perfume | 0.1% | 0.1% | 0.1% | 0.1% |
| Phase B | Sodium Cocoamphoacetate (REWOTERIC ® AM C. Evonik. 32%) | 10.0% | 10.0% | 10.0% | 10.0% |
| Phase C | Water | to 100.0% | to 100.0% | to 100.0% | to 100.0% |
| | Xanthan Gum (Keltrol CG-SFT. CP Kelco) | 1.2% | 1.2% | 1.2% | 1.2% |
| Phase D | Sodium Lauroyl Methyl Isethionate (Iselux. Innospec Active Chemicals) | 4.5% | 4.5% | 4.5% | 4.5% |
| | Capryl/Capramidopropyl Betaine (TEGO ® Betaine 810. Evonik. 38%) | 4.5% | 4.5% | 4.5% | 4.5% |
| | Citric Acid | 1.2% | 1.2% | 1.2% | 1.2% |
| Phase E | Water | 10.0% | 10.0% | 10.0% | 10.0% |
| | Polyquaternium-7 (Merquat 550. Nalco) | 0.4% | 0.4% | 0.4% | 0.4% |
| | Preservative | q.s. | q.s. | q.s. | Body cream |

| Recipes 3a, 3b, 3c and 3d: Shampoo | | | | | |
|---|---|---|---|---|---|
| | | 3a | 3b | 3c | 3d |
| Phase A | Composition from Example 1a | 3.5% | | | |
| | Composition from Example 1c | | 3.5% | | |
| | Composition from Example 1d | | | 3.5% | |
| | Composition from Example 1f | | | | 3.5% |
| | Isopropyl Myristate (TEGOSOFT ® M. Evonik) | 0.2% | 0.2% | 0.2% | 0.2% |
| | Perfume | 0.1% | 0.1% | 0.1% | 0.1% |
| Phase B | Water | to 100.0% | to 100.0% | to 100.0% | to 100.0% |
| Phase C | Sodium Lauryl Sulfate (Texapon LS 35. BASF. 30%) | 28.0% | 28.0% | 28.0% | 28.0% |
| Phase D | Cocamidopropyl Betaine (TEGO ® Betain F 50. Evonik. 38%) | 9.0% | 9.0% | 9.0% | 9.0% |
| Phase E | Cocamide MEA (REWOMID ® C 212. Evonik) | 2.0% | 2.0% | 2.0% | 2.0% |
| | Xanthan Gum (Keltrol CG-SFT. CP Kelco) | 0.3% | 0.3% | 0.3% | 0.3% |
| | Water | 10.0% | 10.0% | 10.0% | 10.0% |
| Phase F | Water | 10.0% | 10.0% | 10.0% | 10.0% |
| | Polyquaternium-10 (Polymer JR 400. Amerchol) | 0.2% | 0.2% | 0.2% | 0.2% |
| Phase G | Citric Acid | to pH 5.0 | to pH 5.0 | to pH 5.0 | to pH 5.0 |
| Phase H | Preservative | q.s. | q.s. | q.s. | Body cream |

| Recipes 4a, 4b, 4c and 4d: Shampoo | | | | |
|---|---|---|---|---|
| Recipes | 4a | 4b | 4c | 4d |
| Water | to 100.0% | to 100.0% | to 100.0% | to 100.0% |
| Composition from Example 1a | 2.5% | 2.5% | | |
| Composition from Example 1c | 1.5% | 1.5% | | |
| Composition from Example 1d | | | 2.5% | 2.5% |
| Composition from Example 1f | | | 1.5% | 1.5% |
| Cocamidopropyl Betaine (TEGO ® Betain F 50. Evonik. 38%) | 22.0% | 22.0% | 22.0% | 22.0% |
| Lauryl Glucoside (Plantacare 1200 UP. BASF. 50%) | 6.0% | 6.0% | 6.0% | 6.0% |
| Sodium Cocoyl Glutamate (Plantapon ACG HC. BASF) | 1.5% | 1.5% | 1.5% | 1.5% |
| Sodium Cocoyl Glycinate (Hostapon SG. Clariant) | 0.8% | 0.8% | 0.8% | 0.8% |
| Zinc Pyrithione (Microcare ZP. Thor) | 0.1% | 0.1% | 0.1% | 0.1% |
| PEG-120 Methyl Glucose Dioleate (ANTIL ® 120 Plus. Evonik) | 0.4% | 0.4% | 0.4% | 0.4% |
| Sodium Chloride | 0.5% | 0.5% | 0.5% | 0.5% |
| Isostearamide MIPA; Glyceryl Laurate (ANTIL ® SPA 80. Evonik) | 0.5% | 0.5% | 0.5% | 0.5% |
| Xanthan Gum (Keltrol CG-SFT. CP Kelco) | 0.3% | 0.3% | 0.3% | 0.3% |
| Hydroxypropyl Guar Hydroxypropyltrimonium Chloride (Jaguar C-162. Solvay Rhodia) | 0.3% | 0.3% | 0.3% | 0.3% |
| Quaternium-80 (ABIL ® Quat 3272. Evonik) | 0.4% | 0.4% | 0.4% | 0.4% |
| Palmitamidopropyltrimonium Chloride (VARISOFT ® PATC. Evonik) | 0.4% | 0.4% | 0.4% | 0.4% |
| *Argania Spinosa* Oil (Argan Oil. DSM Nutritional Products Ltd.) | 0.1% | 0.1% | 0.1% | 0.1% |
| Glycerol (Glycerol EP. vegetable. Spiga Nord) | 0.6% | 0.6% | 0.6% | 0.6% |
| Tetrasodium EDTA (Versene 100. The Dow Chemical Company) | 0.1% | 0.1% | 0.1% | 0.1% |
| Caffeine (Merck KGaA/EMD Chemicals. Inc.) | 0.1% | 0.1% | 0.1% | 0.1% |
| Hydrolyzed Wheat Protein (Gluadin WLM. BASF) | 0.1% | 0.1% | 0.1% | 0.1% |
| Limonene (Dipentene No. 122. Hercules Inc.) | 0.1% | 0.1% | 0.1% | 0.1% |
| Citric Acid | to pH 5.5 | to pH 5.5 | to pH 5.5 | to pH 5.5 |
| Sodium Phytate; Aqua; Alcohol (dermofeel ® PA-3; Evonik Dr. Straetmans GmbH (PA-3) | | 0.1% | 0.1% | 0.1% |
| Perfume | 0.2% | | | |
| Preservative | q.s. | | | |
| Aqua; Sodium Levulinate; Sodium Benzoate (Verstatil ® BL non GMO; Evonik Dr. Straetmans GmbH) | | 1.2% | 1.2% | 1.2% |

| Recipes 5a, 5b, 5c and 5d: Liquid Soap | | | | |
|---|---|---|---|---|
| | 5a | 5b | 5c | 5d |
| Water | to 100% | to 100% | to 100% | to 100% |
| Glycerol (Glycerol EP. vegetable. Spiga Nord) | 4.0% | 4.0% | 4.0% | 4.0% |
| Alcohol | 4.0% | 4.0% | 4.0% | 4.0% |
| Sodium Coco-Sulfate (Texapon HC G. BASF) | 3.0% | 3.0% | 3.0% | 3.0% |
| Lauryl Glucoside (Plantacare 1200 UP. BASF. 50%) | 6.0% | 6.0% | 6.0% | 6.0% |
| Composition from Example 1a | 0.1% | | | |
| Composition from Example 1c | | 0.1% | | |
| Composition from Example 1d | | | 0.1% | |
| Composition from Example 1f | | | | 0.1% |
| Xanthan Gum (Keltrol CG-SFT. CP Kelco) | 1.5% | 1.5% | 1.5% | 1.5% |
| *Mangifera Indica* (Mango) Fruit Extract (Mango Extract. Draco Natural Products) | 0.5% | 0.5% | 0.5% | 0.5% |
| Limonene (Dipentene No. 122. Hercules Inc.) | 0.1% | 0.1% | 0.1% | 0.1% |
| Linalool (Lipofresh. Lipo Chemicals. Inc.) | 0.1% | 0.1% | 0.1% | 0.1% |
| Citric Acid | to pH 4.9 | to pH 4.9 | to pH 4.9 | to pH 4.9 |
| Preservative | q.s. | q.s. | q.s. | q.s. |
| Dyes | Body cream | q.s. | q.s. | q.s. |

| Recipes 6a, 6b, 6c and 6d: Cream Soap | | | | |
|---|---|---|---|---|
| | 6a | 6b | 6c | 6d |
| Water | to 100% | to 100% | to 100% | to 100% |
| Propylene Glycol (Euxyl K 320. Schülke & Mayr GmbH) | 2.0% | 2.0% | 2.0% | 2.0% |
| Coco-Glucoside (Plantacare 818 UP. BASF. 51%) | 10.0% | 10.0% | 10.0% | 10.0% |
| Glycerol (Glycerol EP. vegetable. Spiga Nord) | 5.0% | 5.0% | 5.0% | 5.0% |
| Composition from Example 1a | 2.5% | | | |
| Composition from Example 1c | | 2.5% | | |
| Composition from Example 1d | | | 2.5% | |
| Composition from Example 1f | | | | 2.5% |
| Disodium Cocoyl Glutamate (Planatpon ACG LC. BASF) | 2.5% | 2.5% | 2.5% | 2.5% |
| Xanthan Gum (Keltrol CG-SFT. CP Kelco) | 1.2% | 1.2% | 1.2% | 1.2% |
| Stearic Acid (Pristerene 4922. Croda Europe. Ltd.) | 1.2% | 1.2% | 1.2% | 1.2% |
| Citric Acid | to pH 5.5 | to pH 5.5 | to pH 5.5 | to pH 5.5 |
| *Olea Europaea* Fruit Oil (Cropure Olive. Croda Europe. Ltd.) | 0.2% | 0.2% | 0.2% | 0.2% |
| Glyceryl Oleate (TEGIN ® O V. Evonik) | 1.0% | 1.0% | 1.0% | 1.0% |
| Sodium Cocoyl Glutamate (Plantapon ACG HC. BASF) | 0.8% | 0.8% | 0.8% | 0.8% |
| Tetrasodium EDTA (Versene 100. The Dow Chemical Company) | 0.2% | 0.2% | 0.2% | 0.2% |
| Perfume | 0.1% | 0.1% | 0.1% | 0.1% |
| Preservative | q.s. | q.s. | q.s. | q.s. |
| Dyes | q.s. | q.s. | q.s. | Body cream |

| Recipes 7a, 7b, 7c and 7d: Oil Bath | | | | |
|---|---|---|---|---|
| | 7a | 7b | 7c | 7d |
| Water | to 100.0% | to 100.0% | to 100.0% | to 100.0% |
| *Glycine Soja* Oil (Cropure Soybean. Croda Europe. Ltd.) | 20.0% | 20.0% | 20.0% | 20.0% |
| Composition from Example 1a | 12.0% | | | |
| Composition from Example 1c | | 12.0% | | |
| Composition from Example 1d | | | 12.0% | |
| Composition from Example 1f | | | | 12.0% |
| Polyglyceryl-3 Palmitate (Dermofeel ® PP. Evonik Dr. Straetmans) | 4.5% | 4.5% | 4.5% | 4.5% |
| Glyceryl Caprylate (Dermosoft ® GMCY. Evonik Dr. Straetmans) | 3.0% | 3.0% | 3.0% | 3.0% |

-continued

| Recipes 7a, 7b, 7c and 7d: Oil Bath | | | | |
|---|---|---|---|---|
| | 7a | 7b | 7c | 7d |
| *Simmondsia Chinensis* Seed Oil (AEC Jojoba Oil Refined. A & E Connock. Perfumery & Cosmetics Ltd.) | 1.2% | 1.2% | 1.2% | 1.2% |
| *Prunus Amygdalus* Dulcis (Sweet Almond) Oil (Cropure Almond. Croda Europe. Ltd.) | 1.0% | 1.0% | 1.0% | 1.0% |
| *Triticum Vulgare* Germ Oil (Cropure Wheatgerm. Croda Europe. Ltd.) | 0.5% | 0.5% | 0.5% | 0.5% |
| Tocopherol (Euxyl K 700. Schülke & Mayr GmbH) | 0.2% | 0.2% | 0.2% | 0.2% |
| Limonene (Dipentene No. 122. Hercules Inc.) | 0.1% | 0.1% | 0.1% | 0.1% |
| Citral | 0.1% | 0.1% | 0.1% | 0.1% |
| Preservative | q.s. | q.s. | q.s. | q.s. |
| Dyes | q.s. | q.s. | q.s. | q.s. |

| Recipes 8a, 8b, 8c and 8d: Micellar Water for make-up removal | | | | |
|---|---|---|---|---|
| | 8a | 8b | 8c | 8d |
| Water | to 100.0% | to 100.0% | to 100.0% | to 100.0% |
| Perfume | 0.1% | 0.1% | 0.1% | 0.1% |
| Composition from Example 1a | 2.0% | | | |
| Composition from Example 1c | | 2.0% | | |
| Composition from Example 1d | | | 2.0% | |
| Composition from Example 1f | | | | 2.0% |
| Capryl/Capramidopropyl Betaine (TEGO ® Betain 810. Evonik. 38%) | 1.3% | 1.3% | 1.3% | 1.3% |
| Polyglyceryl-6 Caprylate; Polyglyceryl-3 Cocoate; Polyglyceryl-4 Caprate; Polyglyceryl-6 Ricinoleate (TEGO ® Solve 61. Evonik) | 1.0% | 1.0% | 1.0% | 1.0% |
| Betaine (TEGO ® Natural Betaine. Evonik) | 2.0% | 2.0% | 2.0% | 2.0% |
| Glycerol (Glycerol EP. vegetable. Spiga Nord) | 1.0% | 1.0% | 1.0% | 1.0% |
| Preservative | q.s. | q.s. | q.s. | q.s. |

| Recipes 9a, 9b, 9c and 9d: Solution for wet wipes | | | | |
|---|---|---|---|---|
| Recipe | 9a | 9b | 9c | 9d |
| Composition from Example 1a | 3.5% | | | |
| Composition from Example 1c | | 3.5% | | |
| Composition from Example 1d | | | 3.5% | |
| Composition from Example 1f | | | | 3.5% |
| *Aloe Barbadensis* Leaf Extract (Aloe-Con UP 40. Florida Food Products Inc.) | 0.2% | 0.2% | 0.2% | 0.2% |
| Isopropyl Myristate (TEGOSOFT ® M. Evonik) | 0.2% | 0.2% | 0.2% | 0.2% |
| Disodium Cocoamphodiacetate (REWOTERIC ® AM 2 C NM. Evonik. 39%) | 1.5% | 1.5% | 1.5% | 1.5% |
| Perfume | 0.2% | 0.2% | 0.2% | 0.2% |
| Propylene Glycol (Euxyl K 320. Schülke & Mayr GmbH) | 2.5% | 2.5% | 2.5% | 2.5% |
| Hydrolyzed Silk (Crosilk 10000. Croda Inc.) | 0.2% | 0.2% | 0.2% | 0.2% |
| Caprylyl/Capryl Glucoside (Plantacare 810 UP. BASF) | 1.0% | 1.0% | 1.0% | 1.0% |
| Water | to 100.0% | to 100.0% | to 100.0% | to 100.0% |
| Citric Acid | to pH 5.0 | to pH 5.0 | to pH 5.0 | to pH 5.0 |
| Phenoxyethanol (S&M Phenoxyethanol. Schülke & Mayr GmbH) | 0.5% | 0.5% | 0.5% | 0.5% |
| Dehydroacetic Acid (Unisept DHA (Universal Preserv-A-Chem. Inc.) | 0.1% | 0.1% | 0.1% | 0.1% |
| Sodium Benzoate (Euxyl K 712. Schülke & Mayr GmbH) | 0.4% | 0.4% | 0.4% | 0.4% |
| Salicylic Acid (Salicylic acid nat.; Evonik Dr. Straetmans GmbH) | 0.5% | 0.5% | 0.5% | 0.5% |

| Recipes 10a, 10b, 10c and 10d: Antiperspirant deodorant | | | | | |
|---|---|---|---|---|---|
| | | 10a | 10b | 10c | 10d |
| Phase A | Composition from Example 1a | 4.0% | | | |
| | Composition from Example 1c | | 4.0% | | |
| | Composition from Example 1d | | | 4.0% | |
| | Composition from Example 1f | | | | 4.0% |
| | Dicaprylyl Ether (Cetiol OE. BASF) | 0.3% | 0.3% | 0.3% | 0.3% |
| | Geraniol (Nerol 800. International Flavors & Fragrances Inc.) | 0.1% | 0.1% | 0.1% | 0.1% |
| | Linalool (Lipofresh. Lipo Chemicals. Inc.) | 0.1% | 0.1% | 0.1% | 0.1% |
| | Perfume | 0.1% | 0.1% | 0.1% | 0.1% |
| Phase B | Propylene Glycol (Euxyl K 320. Schülke & Mayr GmbH) | 1.0% | 1.0% | 1.0% | 1.0% |
| | Butylene Glycol (Oxea Corparation) | 0.2% | 0.2% | 0.2% | 0.2% |
| | Water | 5.0% | 5.0% | 5.0% | 5.0% |
| | Palmitamidopropyltrimonium Chloride (VARISOFT ® PATC. Evonik) | 1.0% | 1.0% | 1.0% | 1.0% |
| Phase C | Water | 50.0% | 50.0% | 50.0% | 50.0% |
| | Hydroxethyl Ethylcellulose (Structure Cel 4400 E. AkzoNobel) | 0.8% | 0.8% | 0.8% | 0.8% |
| | Sodium Hydroxide (10% in water) | 0.3% | 0.3% | 0.3% | 0.3% |
| Phase D | Aluminium Chlorohydrate (Locron L. Clariant) | 15.0% | 15.0% | 15.0% | 15.0% |
| Phase E | Preservative | q.s. | q.s. | q.s. | q.s. |
| | Water | to 100.0% | to 100.0% | to 100.0% | to 100.0% |

| Recipes 11a, 11b, 11c and 11d: Mouthwash | | | | |
|---|---|---|---|---|
| | 11a | 11b | 11c | 11d |
| Composition from Example 1a | 0.4% | | | |
| Composition from Example 1c | | 0.4% | | |
| Composition from Example 1d | | | 0.4% | |
| Composition from Example 1f | | | | 0.4% |
| Glycolipids (Rheance One. Evonik) | 0.2% | 0.2% | 0.2% | 0.2% |
| Flavor | 0.2% | 0.2% | 0.2% | 0.2% |
| Water | to 100.0% | to 100.0% | to 100.0% | to 100.0% |
| Sorbitol (Karion FP Liquid. Merck) | 3.0% | 3.0% | 3.0% | 3.0% |
| Preservative | q.s. | q.s. | q.s. | q.s. |
| Dyes | q.s. | q.s. | q.s. | q.s. |

| Recipes 12a, 12b, 12c and 12d: Toothpaste | | | | | |
|---|---|---|---|---|---|
| | | 12a | 12b | 12c | 12d |
| A | Sorbitol (Karion FP Liquid. Merck) | 50.0% | 50.0% | 50.0% | 50.0% |
| | Water | to 100.0% | to 100.0% | to 100.0% | to 100.0% |
| | Sodium Carboxymethylcelluslose (Blanose 7MXF. Ashland) | 1.2% | 1.2% | 1.2% | 1.2% |
| B | Sodium Saccharine (Sigma Aldrich) | 0.1% | 0.1% | 0.1% | 0.1% |
| | Sodium Fluoride (Sigma Aldrich) | 0.1% | 0.1% | 0.1% | 0.1% |
| C | Titanium Dioxide (Caesar & Loretz) | 0.4% | 0.4% | 0.4% | 0.4% |
| | Hydrated Silica (Zeodent ® 113. Evonik) | 14.0% | 14.0% | 14.0% | 14.0% |
| | Hydrated Silica (Zeodent ® 165. Evonik) | 8.0% | 8.0% | 8.0% | 8.0% |
| D | Flavor oil | 1.0% | 1.0% | 1.0% | 1.0% |
| E | Glyceryl Caprylate (dermosoft ® GMCY. Evonik) | 0.3% | 0.3% | 0.3% | 0.3% |
| | Composition from Example 1a | 3.5% | | | |
| | Composition from Example 1c | | 3.5% | | |
| | Composition from Example 1d | | | 3.5% | |
| | Composition from Example 1f | | | | 3.5% |

| Recipes 13a, 13b, 13c and 13d: Kitchen Cleaning Spray | | | | |
|---|---|---|---|---|
| Ingredient | 13a | 13b | 13c | 13d |
| REWOTERIC ® AM V | 0.5% | 0.5% | 0.5% | 0.5% |
| Composition from Example 1a | 1.0% | | | |
| Composition from Example 1c | | 1.0% | | |
| Composition from Example 1d | | | 1.0% | |
| Composition from Example 1f | | | | 1.0% |
| TOMAKLEEN ® G-14 | 2.0% | 2.0% | 2.0% | 2.0% |
| Water (Dye. Perfume) | 89.5% | 89.5% | 89.5% | 89.5% |
| Chelating Agent. GLDA | 3.0% | 3.0% | 3.0% | 3.0% |
| Triethanolamine | 4.0% | 4.0% | 4.0% | 4.0% |

| Recipes 14a, 14b, 14c and 14d: Extra Mild Dish Wash Foam | | | | |
|---|---|---|---|---|
| Ingredient | 14a | 14b | 14c | 14d |
| C10-16 Alkylpolyglucoside. 50% | 10.0% | 10.0% | 10.0% | 10.0% |
| Xanthan Gum | 0.1% | 0.1% | 0.1% | 0.1% |
| Glycerin | 2.0% | 2.0% | 2.0% | 2.0% |
| Water | 76.9% | 76.9% | 76.9% | 76.9% |
| Composition from Example 1a | 1.0% | | | |
| Composition from Example 1c | | 1.0% | | |
| Composition from Example 1d | | | 1.0% | |
| Composition from Example 1f | | | | 1.0% |
| REWOFERM ® SL ONE | 2.0% | 2.0% | 2.0% | 2.0% |
| REWOPOL ® SB CS 50 | 5.0% | 5.0% | 5.0% | 5.0% |
| TEGO ® Betain C 60 | 3.0% | 3.0% | 3.0% | 3.0% |
| Preservative | qs. | qs. | qs. | qs. |

| Recipes 15a, 15b, 15c and 15d: Automatic Rinse Aid for Direct Use 1 | | | | |
|---|---|---|---|---|
| Ingredient | 15a | 15b | 15c | 15d |
| TEGOTENS ® EC 11 | 5.0% | 5.0% | 5.0% | 5.0% |
| Composition from Example 1a | 5.0% | | | |
| Composition from Example 1c | | 5.0% | | |
| Composition from Example 1d | | | 5.0% | |
| Composition from Example 1f | | | | 5.0% |
| Citric acid monohydrate | 5.0% | 5.0% | 5.0% | 5.0% |
| Water (Dye. Perfume) | 85.0% | 85.0% | 85.0% | 85.0% |

| Recipes 16a, 16b, 16c and 16d: Automatic Rinse Aid for Direct Use 2 | | | | |
|---|---|---|---|---|
| Ingredient | 16a | 16b | 16c | 16d |
| Citric acid monohydrate | 5.0% | 5.0% | 5.0% | 5.0% |
| Sodium Cumene Sulfonate. 92% | 1.5% | 1.5% | 1.5% | 1.5% |
| Water (Dye. Perfume) | 83.5% | 83.5% | 83.5% | 83.5% |
| TEGOTENS ® EC 11 | 6.0% | 6.0% | 6.0% | 6.0% |
| Composition from Example 1a | 4.0% | | | |
| Composition from Example 1c | | 4.0% | | |
| Composition from Example 1d | | | 4.0% | |
| Composition from Example 1f | | | | 4.0% |

-continued

| Recipes 17a, 17b, 17c and 17d: Automatic Rinse Aid for Direct Use 3 | | | | |
|---|---|---|---|---|
| Ingredient | 17a | 17b | 17c | 17d |
| Citric acid monohydrate | 5.0% | 5.0% | 5.0% | 5.0% |
| Sodium Cumene Sulfonate. 92% | 1.5% | 1.5% | 1.5% | 1.5% |
| Water (Dye. Perfume) | 83.5% | 83.5% | 83.5% | 83.5% |
| TEGOTENS ® EC 11 | 7.0% | 7.0% | 7.0% | 7.0% |
| Composition from Example 1a | 3.0% | | | |
| Composition from Example 1c | | 3.0% | | |
| Composition from Example 1d | | | 3.0% | |
| Composition from Example 1f | | | | 3.0% |

| Recipes 18a, 18b, 18c and 18d: Glass Cleaner With Optimized Antifogging Efficiency | | | | |
|---|---|---|---|---|
| Ingredient | 18a | 18b | 18c | 18d |
| REWOPOL ® TS 35 | 1.0% | 1.0% | 1.0% | 1.0% |
| Composition from Example 1a | 0.2% | | | |
| Composition from Example 1c | | 0.2% | | |
| Composition from Example 1d | | | 0.2% | |
| Composition from Example 1f | | | | 0.2% |
| Isopropanol | 15.0% | 15.0% | 15.0% | 15.0% |
| Chelating Agent. M | 2.0% | 2.0% | 2.0% | 2.0% |
| Water (Dye. Perfume) | 81.8% | 81.8% | 81.8% | 81.8% |

| Recipes 19a, 19b, 19c and 19d: Oven Cleanser for Smoking Chamber | | | | |
|---|---|---|---|---|
| Ingredient | 19a | 19b | 19c | 19d |
| Water | 77.6% | 77.6% | 77.6% | 77.6% |
| Trilon A liquid | 8.0% | 8.0% | 8.0% | 8.0% |
| Sodium carbonate | 6.0% | 6.0% | 6.0% | 6.0% |
| REWOTERIC ® AM KSF 40 | 5.0% | 5.0% | 5.0% | 5.0% |
| Laureth-6 | 1.2% | 1.2% | 1.2% | 1.2% |
| Composition from Example 1a | 1.2% | | | |
| Composition from Example 1c | | 1.2% | | |
| Composition from Example 1d | | | 1.2% | |
| Composition from Example 1f | | | | 1.2% |
| DOWANOL DPnB | 1.0% | 1.0% | 1.0% | 1.0% |

| Recipes 20a, 20b, 20c and 20d: All Purpose Cleanser (Microemulsion) | | | | |
|---|---|---|---|---|
| Ingredient | 20a | 20b | 20c | 20d |
| Water | 73.0% | 73.0% | 73.0% | 73.0% |
| TEGOTENS ® AM VSF | 6.0% | 6.0% | 6.0% | 6.0% |
| Composition from Example 1a | 2.0% | | | |
| Composition from Example 1c | | 2.0% | | |
| Composition from Example 1d | | | 2.0% | |
| Composition from Example 1f | | | | 2.0% |
| REWOPOL ® D 510 NC | 5.0% | 5.0% | 5.0% | 5.0% |
| Undeceth-6 | 3.0% | 3.0% | 3.0% | 3.0% |
| Potassium hydroxide. 50% | 5.0% | 5.0% | 5.0% | 5.0% |
| Chelating Agent. MGDA | 6.0% | 6.0% | 6.0% | 6.0% |

| Recipes 21a, 21b, 21c and 21d: Low Foaming Hard Surface Degreaser | | | | |
|---|---|---|---|---|
| Ingredient | 21a | 21b | 21c | 21d |
| C9-11 FATTY ALCOHOL ETHOXYLATE - 8 MOLES OF EO | 2.0% | 2.0% | 2.0% | 2.0% |
| Composition from Example 1a | 1.0% | | | |
| Composition from Example 1c | | 1.0% | | |
| Composition from Example 1d | | | 1.0% | |

-continued

| Recipes 21a, 21b, 21c and 21d: Low Foaming Hard Surface Degreaser | | | | |
|---|---|---|---|---|
| Ingredient | 21a | 21b | 21c | 21d |
| Composition from Example 1f | | | | 1.0% |
| TEGOTENS ® G 826 C | 4.0% | 4.0% | 4.0% | 4.0% |
| Chelating Agent. MGDA | 7.5% | 7.5% | 7.5% | 7.5% |
| Water (Dye. Perfume) | 85.5% | 85.5% | 85.5% | 85.5% |

| Recipes 22a, 22b, 22c and 22d: Low Foaming Hard Surface Degreaser (101630-23) | | | | |
|---|---|---|---|---|
| Ingredient | 22a | 22b | 22c | 22d |
| C9-11 FATTY ALCOHOL ETHOXYLATE - 8 MOLES OF EO | 2.0% | 2.0% | 2.0% | 2.0% |
| Composition from Example 1a | 1.0% | | | |
| Composition from Example 1c | | 1.0% | | |
| Composition from Example 1d | | | 1.0% | |
| Composition from Example 1f | | | | 1.0% |
| TEGOTENS ® G 826 C | 4.0% | 4.0% | 4.0% | 4.0% |
| Chelating Agent. MGDA | 7.5% | 7.5% | 7.5% | 7.5% |
| Water (Dye. Perfume) | 85.5% | 85.5% | 85.5% | 85.5% |

| Recipes 23a, 23b, 23c and 23d: Foaming Hard Surface Degreaser 1 | | | | |
|---|---|---|---|---|
| Ingredient | 23a | 23b | 23c | 23d |
| C9-11 FATTY ALCOHOL ETHOXYLATE - 8 MOLES OF EO | 2.0% | 2.0% | 2.0% | 2.0% |
| TEGOTENS ® AM VSF | 6.0% | 6.0% | 6.0% | 6.0% |
| Composition from Example 1a | 1.0% | | | |
| Composition from Example 1c | | 1.0% | | |
| Composition from Example 1d | | | 1.0% | |
| Composition from Example 1f | | | | 1.0% |
| Chelating Agent. MGDA | 7.5% | 7.5% | 7.5% | 7.5% |
| Water (Dye. Perfume) | 83.5% | 83.5% | 83.5% | 83.5% |

| Recipes 24a, 24b, 24c and 24d: Foaming Hard Surface Degreaser 2 | | | | |
|---|---|---|---|---|
| Ingredient | 24a | 24b | 24c | 24d |
| C9-11 FATTY ALCOHOL ETHOXYLATE - 8 MOLES OF EO | 3.0% | 3.0% | 3.0% | 3.0% |
| REWOTERIC ® AM KSF 40 | 2.5% | 2.5% | 2.5% | 2.5% |
| Composition from Example 1a | 1.0% | | | |
| Composition from Example 1c | | 1.0% | | |
| Composition from Example 1d | | | 1.0% | |
| Composition from Example 1f | | | | 1.0% |
| Chelating Agent. MGDA | 10.0% | 10.0% | 10.0% | 10.0% |
| Water (Dye. Perfume) | 83.5% | 83.5% | 83.5% | 83.5% |

| Recipes 25a, 25b, 25c and 25d: Low Foaming Hard Surface Degreaser | | | | |
|---|---|---|---|---|
| Ingredient | 25a | 25b | 25c | 25d |
| Composition from Example 1a | 1.0% | | | |
| Composition from Example 1c | | 1.0% | | |
| Composition from Example 1d | | | 1.0% | |
| Composition from Example 1f | | | | 1.0% |
| C8-10 Alkylpolyglucosid | 4.0% | 4.0% | 4.0% | 4.0% |
| Sodium C13-17 Alkane Sulfonate. 30% | 2.0% | 2.0% | 2.0% | 2.0% |
| Chelating Agent. MGDA | 7.5% | 7.5% | 7.5% | 7.5% |
| Water (Dye. Perfume) | 85.5% | 85.5% | 85.5% | 85.5% |

| Recipes 26a, 26b, 26c and 26d: Hard Surface Degreaser From Renewable Surfactants | | | | |
|---|---|---|---|---|
| Ingredient | 26a | 26b | 26c | 26d |
| Water | 89.3% | 89.3% | 89.3% | 89.3% |
| Chelating Agent. MGDA | 4.0% | 4.0% | 4.0% | 4.0% |
| Sodium carbonate | 3.0% | 3.0% | 3.0% | 3.0% |
| TEGOTENS ® AM VSF | 2.4% | 2.4% | 2.4% | 2.4% |
| Laureth-6 | 0.6% | 0.6% | 0.6% | 0.6% |
| Composition from Example 1a | 0.4% | | | |
| Composition from Example 1c | | 0.4% | | |
| Composition from Example 1d | | | 0.4% | |
| Composition from Example 1f | | | | 0.4% |
| TEGO ® Polish Additiv Q 70 | 0.3% | 0.3% | 0.3% | 0.3% |

| Recipes 27a, 27b, 27c and 27d: Highly Efficient Floor Cleanser | | | | |
|---|---|---|---|---|
| Ingredient | 27a | 27b | 27c | 27d |
| Water | 89.3% | 89.3% | 89.3% | 89.3% |
| Chelating Agent. MGDA | 4.0% | 4.0% | 4.0% | 4.0% |
| Sodium carbonate | 3.0% | 3.0% | 3.0% | 3.0% |
| TEGOTENS ® AM VSF | 2.4% | 2.4% | 2.4% | 2.4% |
| Laureth-6 | 0.6% | 0.6% | 0.6% | 0.6% |
| Composition from Example 1a | 0.4% | | | |
| Composition from Example 1c | | 0.4% | | |
| Composition from Example 1d | | | 0.4% | |
| Composition from Example 1f | | | | 0.4% |
| TEGO ® Polish Additiv Q 70 | 0.3% | 0.3% | 0.3% | 0.3% |

| Recipes 28a, 28b, 28c and 28d: Super Natural Wash Lotion for Textile Face Masks | | | | |
|---|---|---|---|---|
| Ingredient | 28a | 28b | 28c | 28d |
| Xanthan Gum | 0.1% | 0.1% | 0.1% | 0.1% |
| Glycerin | 2.0% | 2.0% | 2.0% | 2.0% |
| Water | 76.9% | 76.9% | 76.9% | 76.9% |
| Composition from Example 1a | 1.0% | | | |
| Composition from Example 1c | | 1.0% | | |
| Composition from Example 1d | | | 1.0% | |
| Composition from Example 1f | | | | 1.0% |
| REWOFERM ® SL ONE | 2.0% | 2.0% | 2.0% | 2.0% |
| REWOPOL ® SB CS 50 | 5.0% | 5.0% | 5.0% | 5.0% |
| C8-10 Alkylpolyglucosid | 10.0% | 10.0% | 10.0% | 10.0% |
| TEGO ® Betain C 60 | 3.0% | 3.0% | 3.0% | 3.0% |
| Preservative | qs. | qs. | qs. | qs. |

| Recipes 29a, 29b, 29c and 29d: Highly Effective Presoaker | | | | |
|---|---|---|---|---|
| Ingredient | 29a | 29b | 29c | 29d |
| Water | 77.5% | 77.5% | 77.5% | 77.5% |
| Chelating Agent. Mgda | 8.0% | 8.0% | 8.0% | 8.0% |
| Sodium metasilicate | 2.0% | 2.0% | 2.0% | 2.0% |

-continued

| Recipes 29a, 29b, 29c and 29d: Highly Effective Presoaker | | | | |
|---|---|---|---|---|
| Ingredient | 29a | 29b | 29c | 29d |
| Sodium gluconate | 2.0% | 2.0% | 2.0% | 2.0% |
| Sodium carbonate | 2.0% | 2.0% | 2.0% | 2.0% |
| TEGOTENS ® AM VSF | 6.5% | 6.5% | 6.5% | 6.5% |
| Undeceth-6 | 0.6% | 0.6% | 0.6% | 0.6% |
| Composition from Example 1a | 0.4% | | | |
| Composition from Example 1c | | 0.4% | | |
| Composition from Example 1d | | | 0.4% | |
| Composition from Example 1f | | | | 0.4% |
| DOWANOL DPnB | 1.0% | 1.0% | 1.0% | 1.0% |

| Recipes 30a, 30b, 30c and 30d: Presoaker (Basic Formula) | | | | |
|---|---|---|---|---|
| Ingredient | 30a | 30b | 30c | 30d |
| Water | 82.6% | 82.6% | 82.6% | 82.6% |
| Trilon A 92 | 3.0% | 3.0% | 3.0% | 3.0% |
| Sodium metasilicate | 2.0% | 2.0% | 2.0% | 2.0% |
| Sodium carbonate | 2.0% | 2.0% | 2.0% | 2.0% |
| Bayhibit AM | 1.0% | 1.0% | 1.0% | 1.0% |
| REWOTERIC ® AM KSF 40 | 4.0% | 4.0% | 4.0% | 4.0% |
| C9-11 FATTY ALCOHOL ETHOXYLATE - 8 MOLES OF EO | 1.2% | 1.2% | 1.2% | 1.2% |
| Composition from Example 1a | 1.2% | | | |
| Composition from Example 1c | | 1.2% | | |
| Composition from Example 1d | | | 1.2% | |
| Composition from Example 1f | | | | 1.2% |
| DOWANOL DPnB | 3.0% | 3.0% | 3.0% | 3.0% |

| Recipes 31a, 31b, 31c and 31d: Good Dispersing Presoaker | | | | |
|---|---|---|---|---|
| Ingredient | 31a | 31b | 31c | 31d |
| Water | 80.0% | 80.0% | 80.0% | 80.0% |
| Trilon A 92 | 3.0% | 3.0% | 3.0% | 3.0% |
| Sodium metasilicate | 2.0% | 2.0% | 2.0% | 2.0% |
| Sodium carbonate | 2.0% | 2.0% | 2.0% | 2.0% |
| Sequion 10 Na 430 | 2.0% | 2.0% | 2.0% | 2.0% |
| TEGOTENS ® 475 | 5.0% | 5.0% | 5.0% | 5.0% |
| C9-11 FATTY ALCOHOL ETHOXYLATE - 7 MOLES OF EO | 1.5% | 1.5% | 1.5% | 1.5% |
| Composition from Example 1a | 1.5% | | | |
| Composition from Example 1c | | 1.5% | | |
| Composition from Example 1d | | | 1.5% | |
| Composition from Example 1f | | | | 1.5% |
| DOWANOL PnB | 3.0% | 3.0% | 3.0% | 3.0% |

| Recipes 32a, 32b, 32c and 32d: Cost Efficient Presoaker | | | | |
|---|---|---|---|---|
| Ingredient | 32a | 32b | 32c | 32d |
| Water | 80.5% | 80.5% | 80.5% | 80.5% |
| Chelating Agent. M | 8.0% | 8.0% | 8.0% | 8.0% |
| Sodium carbonate | 6.0% | 6.0% | 6.0% | 6.0% |
| TEGOTENS ® AM VSF | 3.5% | 3.5% | 3.5% | 3.5% |
| Laureth-6 | 0.6% | 0.6% | 0.6% | 0.6% |
| Composition from Example 1a | 0.4% | | | |
| Composition from Example 1c | | 0.4% | | |
| Composition from Example 1d | | | 0.4% | |
| Composition from Example 1f | | | | 0.4% |
| DOWANOL DPnB | 1.0% | 1.0% | 1.0% | 1.0% |

| Recipes 33a, 33b, 33c and 33d: Rinse Aid to minimize remaining water | | | | |
|---|---|---|---|---|
| Ingredient | 33a | 33b | 33c | 33d |
| REWOPAL ® MPG 40 | 6.0% | 6.0% | 6.0% | 6.0% |
| Butyl Cellusolve (BG) | 14.0% | 14.0% | 14.0% | 14.0% |
| Composition from Example 1a | 3.0% | | | |
| Composition from Example 1c | | 3.0% | | |
| Composition from Example 1d | | | 3.0% | |
| Composition from Example 1f | | | | 3.0% |
| REWOQUAT ® CR 3099 | 10.0% | 10.0% | 10.0% | 10.0% |
| TEGOSOFT ® OP | 5.0% | 5.0% | 5.0% | 5.0% |
| Water | 62.0% | 62.0% | 62.0% | 62.0% |

| Recipes 34a, 34b, 34c and 34d: Rinse Aid with Optimal Oil Content | | | | |
|---|---|---|---|---|
| Ingredient | 34a | 34b | 34c | 34d |
| DOWANOL DPnB | 8.6% | 8.6% | 8.6% | 8.6% |
| REWOPAL ® MPG 40 | 6.2% | 6.2% | 6.2% | 6.2% |
| REWOQUAT ® CR 3099 | 10.0% | 10.0% | 10.0% | 10.0% |
| REWOCARE ® DOC | 4.0% | 4.0% | 4.0% | 4.0% |
| TEGOSOFT ® OP | 3.0% | 3.0% | 3.0% | 3.0% |
| Composition from Example 1a | 1.0% | | | |
| Composition from Example 1c | | 1.0% | | |
| Composition from Example 1d | | | 1.0% | |
| Composition from Example 1f | | | | 1.0% |
| Water | 66.8% | 66.8% | 66.8% | 66.8% |
| TEGOPREN ® 6923 | 0.4% | 0.4% | 0.4% | 0.4% |

| Recipes 35a, 35b, 35c and 35d: Low Foaming All Purpose Cleaner | | | | |
|---|---|---|---|---|
| Ingredient | 35a | 35b | 35c | 35d |
| Water | 82.0% | 82.0% | 82.0% | 82.0% |
| Trilon A 92 | 3.0% | 3.0% | 3.0% | 3.0% |
| Sodium metasilicate | 2.0% | 2.0% | 2.0% | 2.0% |
| Sodium carbonate | 2.0% | 2.0% | 2.0% | 2.0% |
| Sequion 10 Na 430 | 2.0% | 2.0% | 2.0% | 2.0% |
| TEGOTENS ® 475 | 5.0% | 5.0% | 5.0% | 5.0% |
| C9-11 FATTY ALCOHOL ETHOXYLATE - 7 MOLES OF EO | 1.5% | 1.5% | 1.5% | 1.5% |
| Composition from Example 1a | 1.5% | | | |
| Composition from Example 1c | | 1.5% | | |
| Composition from Example 1d | | | 1.5% | |
| Composition from Example 1f | | | | 1.5% |
| DOWANOL PnB | 1.0% | 1.0% | 1.0% | 1.0% |

| Recipes 36a, 36b, 36c and 36d: Low Foaming Alkaline Cleanser | | | | |
|---|---|---|---|---|
| Ingredient | 36a | 36b | 36c | 36d |
| Water | 85.5% | 85.5% | 85.5% | 85.5% |
| Chelating Agent. M | 4.0% | 4.0% | 4.0% | 4.0% |
| Sodium carbonate | 6.0% | 6.0% | 6.0% | 6.0% |
| TEGOTENS ® AM VSF | 3.5% | 3.5% | 3.5% | 3.5% |
| Laureth-6 | 0.6% | 0.6% | 0.6% | 0.6% |
| Composition from Example 1a | 0.4% | | | |
| Composition from Example 1c | | 0.4% | | |
| Composition from Example 1d | | | 0.4% | |
| Composition from Example 1f | | | | 0.4% |

Recipes 37a, 37b, 37c and 37d: Low Foaming Alkaline Cleaner

| Ingredient | 37a | 37b | 37c | 37d |
|---|---|---|---|---|
| Water | 85.35% | 85.35% | 85.35% | 85.35% |
| TOMAKLEEN G-14 | 0.75% | 0.75% | 0.75% | 0.75% |
| TEGOTENS ® AM VSF | 3.5% | 3.5% | 3.5% | 3.5% |
| Composition from Example 1a | 0.4% | | | |
| Composition from Example 1c | | 0.4% | | |
| Composition from Example 1d | | | 0.4% | |
| Composition from Example 1f | | | | 0.4% |
| Sodium carbonate | 6.0% | 6.0% | 6.0% | 6.0% |
| MGDA-Na3 (40%) | 4.0% | 4.0% | 4.0% | 4.0% |

Recipes 38a, 38b, 38c and 38d: Alkaline Cleanser (Automatic Wash)

| Ingredient | 38a | 38b | 38c | 38d |
|---|---|---|---|---|
| Water | 59.0% | 59.0% | 59.0% | 59.0% |
| Tetra Potassium Pyrophosphate (TKPP) | 15.0% | 15.0% | 15.0% | 15.0% |
| Trilon A liquid | 5.0% | 5.0% | 5.0% | 5.0% |
| KOH. 45% | 4.0% | 4.0% | 4.0% | 4.0% |
| Sequion 10 Na 430 | 10.0% | 10.0% | 10.0% | 10.0% |
| Sodium metasilicate | 6.0% | 6.0% | 6.0% | 6.0% |
| Composition from Example 1a | 1.0% | | | |
| Composition from Example 1c | | 1.0% | | |
| Composition from Example 1d | | | 1.0% | |
| Composition from Example 1f | | | | 1.0% |

Recipes 39a, 39b, 39c and 39d: Metal Cleaner

| Ingredient | 39a | 39b | 39c | 39d |
|---|---|---|---|---|
| Water | 82.0% | 82.0% | 82.0% | 82.0% |
| TOMAKLEEN ® G-14 | 12.0% | 12.0% | 12.0% | 12.0% |
| REWOTERIC ® AM V | 1.5% | 1.5% | 1.5% | 1.5% |
| Composition from Example 1a | 3.0% | | | |
| Composition from Example 1c | | 3.0% | | |
| Composition from Example 1d | | | 3.0% | |
| Composition from Example 1f | | | | 3.0% |
| Triethanolamine | 1.5% | 1.5% | 1.5% | 1.5% |

Recipes 40a, 40b, 40c and 40d: Metal Cleanser

| Ingredient | 40a | 40b | 40c | 40d |
|---|---|---|---|---|
| Water (Dye. Perfume) | 82.0% | 82.0% | 82.0% | 82.0% |
| Triethanolamine | 1.5% | 1.5% | 1.5% | 1.5% |
| DOWANOL PnP | 6.0% | 6.0% | 6.0% | 6.0% |
| REWOTERIC ® AM V | 1.5% | 1.5% | 1.5% | 1.5% |
| Composition from Example 1a | 3.0% | | | |
| Composition from Example 1c | | 3.0% | | |
| Composition from Example 1d | | | 3.0% | |
| Composition from Example 1f | | | | 3.0% |
| C8-10 Fatty alcohol•5 EO | 6.0% | 6.0% | 6.0% | 6.0% |

Recipes 41a, 41b, 41c and 41d: Cost Efficient Facade Cleanser

| Ingredient | 41a | 41b | 41c | 41d |
|---|---|---|---|---|
| Water | 86.6% | 86.6% | 86.6% | 86.6% |
| Chelating Agent. MGDA | 4.0% | 4.0% | 4.0% | 4.0% |
| Sodium carbonate | 6.0% | 6.0% | 6.0% | 6.0% |
| TEGOTENS ® AM VSF | 2.4% | 2.4% | 2.4% | 2.4% |
| Laureth-6 | 0.6% | 0.6% | 0.6% | 0.6% |
| Composition from Example 1a | 0.4% | | | |
| Composition from Example 1c | | 0.4% | | |
| Composition from Example 1d | | | 0.4% | |
| Composition from Example 1f | | | | 0.4% |

Recipes 42a, 42b, 42c and 42d: Anti-dust Glass and Window Cleaner 1

| Ingredient | 42a | 42b | 42c | 42d |
|---|---|---|---|---|
| Water | ad. 100 | ad. 100 | ad. 100 | ad. 100 |
| Ethanol | 15% | 15% | 15% | 15% |
| Rewoferm RL 100 | 2% | 2% | 2% | 2% |
| Rewocare 755 | 0.5% | 0.5% | 0.5% | 0.5% |
| Composition from Example 1a | 0.1% | | | |
| Composition from Example 1c | | 0.1% | | |
| Composition from Example 1d | | | 0.1% | |
| Composition from Example 1f | | | | 0.1% |
| 2-Phenoxyethanol | 0.1% | 0.1% | 0.1% | 0.1% |
| pH Wert (adjust to) | 8 | 8 | 8 | 8 |

Recipes 43a, 32b, 43c and 43d: Anti-dust Glass and Window Cleaner 2

| Ingredient | 43a | 43b | 43c | 43d |
|---|---|---|---|---|
| Water | ad. 100 | ad. 100 | ad. 100 | ad. 100 |
| Ethanol | 15% | 15% | 15% | 15% |
| Rewoferm RL 100 | | | | |
| Rewocare 755 | 0.5% | 0.5% | 0.5% | 0.5% |
| Composition from Example 1a | 0.1% | | | |
| Composition from Example 1c | | 0.1% | | |
| Composition from Example 1d | | | 0.1% | |
| Composition from Example 1f | | | | 0.1% |
| Rewoferm SL one | 1% | 1% | 1% | 1% |
| Tegotens AM VSF | 1% | 1% | 1% | 1% |
| 2-Phenoxyethanol | 0.1% | 0.1% | 0.1% | 0.1% |
| pH Wert (adjust to) | 8.00 | 8.00 | 8.00 | 8.00 |

Recipes 44: Anti-dust Glass and Window Cleaner 3

| Ingredient | 44 |
|---|---|
| Water | ad. 100 |
| Ethanol | 3% |
| Composition from Example 1f | 0.1% |
| Rewoferm SL one | 1% |
| Tegotens DO 40 | 1% |
| Tegopren 5840 | 0.05% |
| 2-Phenoxyethanol | 0.1% |
| pH Wert (adjust to) | 6.0-7.0 |

Recipes 45, 46, 47: All-purpose Cleaner concentrate

| Ingredient | 45 | 46 | 47 |
|---|---|---|---|
| Water | ad. 100 | ad. 100 | ad. 100 |
| Ethanol | 3% | 3% | 5% |
| Rewoferm RL 100 | | | 2% |
| Tego Betain Powder MB | | 1% | |
| Rewocare 755 | 0.5% | 0.5% | |
| Rewopol SB DO 75 | 3% | | 1.5% |
| Rewoferm SL ONE | 1% | 1% | |

-continued

| Recipes 45, 46, 47: All-purpose Cleaner concentrate | | | |
|---|---|---|---|
| Ingredient | 45 | 46 | 47 |
| Composition from Example 1e | 0.2% | 0.5% | 0.5% |
| Tegotens AM VSF | | 3% | |
| 2-Phenoxyethanol | 0.1% | 0.1% | 0.1% |
| pH Wert (adjust to) | 8 | 8 | 8 |

| Recipes 48, 49, 50: All-purpose Cleaner Cleaner Trigger spray | | | |
|---|---|---|---|
| Ingredient | 48 | 49 | 50 |
| Water | ad. 100 | ad. 100 | ad. 100 |
| Ethanol | 3% | 3% | 3% |
| Rewoferm RL 100 | | 3% | 1.5% |
| Tego Betain Powder MB | | | 1% |
| Rewocare 755 | | | 0.5% |
| Rewoferm SL one | 2% | | |
| Composition from Example 1e | 0.2% | 0.5% | 0.5% |
| Tegotens AM VSF | 1% | | |
| 2-Phenoxyethanol | 0.1% | 0.1% | 0.1% |
| pH Wert (adjust to) | 8.00 | 8.00 | 8.00 |

| Recipes 51, 52, 53: Floor Cleaner | | | |
|---|---|---|---|
| Ingredient | 51 | 52 | 53 |
| Water | 93% | 93% | 80% |
| Rewoferm SL one | | | 1% |
| Rewoferm RL 100 | 1% | 1% | |
| Composition from Example 1e | 0.5% | 0.5% | 0.5% |
| Tego PP 1027 | 0.5% | 0.5% | |
| Tego Betain Powder MB | 1% | 1% | 1% |
| Tegotens AM VSF | | | 3% |
| Tomadol 91-6 | 4% | 4% | 4% |
| Rewocare 755 | | | 0.5% |
| 2-Phenoxyethanol | 0.1% | 0.1% | 0.1% |
| pH Wert (adjust to) | 8.00 | 9.00 | 8.00 |

| Recipes 54, 55, 56: Automatic Dish Rinse Aid | | | |
|---|---|---|---|
| Ingredient | 54 | 55 | 56 |
| Water | ad. 100 | ad. 100 | ad. 100 |
| Composition from Example 1e | 3% | 3% | 3% |
| Citric acid monohydrate | 5% | 5% | 5% |
| Tomadol 91-6 | 5% | 5% | |
| Tomadol 91-8 | | | 3% |
| Tomadol 1-5 | | | 1.5% |
| pH (adjust to) | 4 | 4 | 4 |

| Recipes 57, 58, 59: Bathroom Cleaner | | | |
|---|---|---|---|
| Ingredient | 57 | 58 | 59 |
| Water | ad. 100 | ad. 100 | ad. 100 |
| Rewoferm RL 100 | | 1.5% | |
| Tego Betain Powder MB | 1.5% | 1.5% | 1.5% |
| Rewocare 755 | 0.5% | 0.5% | |
| Rewopol SB DO 75 | | | 1.5% |
| Rewoferm SL one | 1% | 0.5% | 0.5% |
| Composition from Example 1e | 0.5% | 0.5% | 0.5% |
| Tegotens AM VSF | 3% | 1.5% | |
| Rewoteric AM V | | | 1.5% |
| Tego PP 1027 | | | 0.5% |

-continued

| Recipes 57, 58, 59: Bathroom Cleaner | | | |
|---|---|---|---|
| Ingredient | 57 | 58 | 59 |
| GLDA | | | 0.25 |
| 2-Phenoxyethanol | 0.1% | 0.1% | 0.1% |
| pH Wert (adjust to) | 5.5 | 5.5 | 5.5 |

| Recipes 60, 61, 62: Handdishwash Liquid | | | |
|---|---|---|---|
| Ingredient | 60 | 61 | 62 |
| Water | ad. 100 | ad. 100 | ad. 100 |
| Texapon 70 | 15% | 5% | |
| TEGO Betain C 60 | 4.8% | 3% | 3% |
| REWOFERM SL One | 5.4% | 2% | 2% |
| Composition from Example 1e | 0.5% | 1% | 1% |
| C10-16 APG, 50% | | 10% | 10% |
| NaCl | 1.25% | | |
| Xanthan Gum | | 0.3% | 0.3% |
| Glycerin | | 2% | 2% |
| Rewopol SB CS 50 | | | 5% |
| Preservative | q.s. | q.s. | q.s. |
| pH Wert | 5.5 | 5.5 | 5.5 |

| Recipes 63, 64, 65: Cleaner for Plastic furniture and interieur | | | |
|---|---|---|---|
| Ingredient | 63 | 64 | 65 |
| Water | ad. 100 | ad. 100 | ad. 100 |
| GLDA | 3% | 0.5% | 0.5% |
| Composition from Example 1e | 0.5% | 0.5% | 1% |
| Tego Betain C 60 | 1.5% | | |
| Tomakleen 91-6 | 1.5% | | |
| Rewoquat Q 70 | 0.5% | | |
| Rewopol CC 40 B MB | | 4% | |
| Tegotens DO 40 | | | 3.5% |
| Tegopren 6922 | | 1.2% | 1.2% |
| pH Wert (adjust to) | 9 | 9 | 9 |

| Recipes 66, 67, 68: Grill and Oven Cleaner | | | |
|---|---|---|---|
| Ingredient | 66 | 67 | 68 |
| Water | ad. 100 | ad. 100 | ad. 100 |
| MGDA | 5% | 5% | 5% |
| Sodium Carbonate | 5% | 5% | 5% |
| Rewoteric AM KSF 40 MB | 5% | | |
| Tomadol 91-6 | 1.5% | 1.5% | |
| Composition from Example 1e | 1.2% | 1.5% | 1.5% |
| Dowanol DPnB | 1% | 1% | 1% |
| Rewoquat CQ 200 | | 5% | 5% |
| Tomakleen G-14 | | | 6% |
| pH (adjust to) | 12 | 12 | 12 |

| Recipes 69, 70, 71: Cleaner for Food&Beverage Fatsolve | | | |
|---|---|---|---|
| Ingredient | 69 | 70 | 71 |
| Water | ad. 100 | ad. 100 | ad. 100 |
| Rewoquat CQ 200 | 20% | 12% | 12% |
| Rewoteric AM KSF 40 MB | 10% | | |
| Composition from Example 1e | 5% | 5% | 3% |
| MGDA | 5% | | 5% |
| Sodium Carbonate | 3% | | 3% |
| Tomadol 91-8 | | 5% | |

-continued

| Recipes 69, 70, 71: Cleaner for Food&Beverage Fatsolve | | | |
|---|---|---|---|
| Ingredient | 69 | 70 | 71 |
| Tomadol 1-5 | | 3% | 2% |
| pH Wert (adjust to) | 12 | 12 | 12 |

| Recipes 72, 73, 74: Car Shampoo | | | |
|---|---|---|---|
| Ingredient | 72 | 73 | 74 |
| Water | ad. 100 | ad. 100 | ad. 100 |
| Tomakleen G-14 | 5% | 5% | |
| Rewoteric AM KSF 40 MB | 5% | | |
| Composition from Example 1e | 2% | 2% | 1.5% |
| MGDA | 3% | 2% | 3% |
| Sodium Carbonate | 1% | 2% | |
| Sodium laurylethersulfate, 28% | 10% | | |
| Tomadol 91-6 | | 3% | |
| Rewocare 755 | | 0.5% | 0.5% |
| Tego Betain C 60 | | 2% | 3% |
| Rewoferm RL 100 | | | 5% |
| pH Wert (adjust to) | 9 | 10 | 9 |

| Recipes 72, 73, 74: Car Rinse | | | |
|---|---|---|---|
| Ingredient | 72 | 73 | 74 |
| Water | ad. 100 | ad. 100 | ad. 100 |
| Carspray 90 MB | 20% | | |
| Rewopol MPG 40 | | 5% | 5% |
| Composition from Example 1e | 0.5% | 0.5% | 1% |
| Rewoquat CR 3099 | | 15% | |
| Tegopren 6922 | | | 20% |
| Isopropanol | 2% | 2% | 2% |
| pH Wert (adjust to) | 8 | 8 | 8 |

| Recipe 75, Automatic Dish Wash Powder | |
|---|---|
| Ingredient | 75 |
| Sodium carbonate | 42.0% |
| Sodium sulphate | 20.0% |
| Sodium citrate | 15.0% |
| Sodium percarbonate | 10.0% |
| Polymer | 3.0% |
| Phosphonate (HEDP) | 2.5% |
| Sodium metasilicate | 2.0% |
| Tomakleen G-14 | 1.0% |
| Composition from Example 1e | 1.0% |
| TAED | 2.0% |
| Protease | 1.0% |
| Amylase | 0.5% |

| Recipe 76, Automatic Dish Wash Gel | |
|---|---|
| Ingredient | 76 |
| Water | 65% |
| Tetrasodium Glutamare diacetate/GLDA | 16% |
| Glycerol | 9.0% |
| Polyacrylate polymer | 2.0% |
| Protease | 1.0% |
| Formic acid | 0.2% |
| PPG-1 C6-10 Pareth-20 | 2.0% |
| Amylase | 0.50% |
| Xanthan Gum | 0.50% |
| Composition from Example 1e | 0.25% |
| Perfumes | 0.20% |
| Zinc acetate dihydrate | 0.10% |
| Calcium Chloride | 0.10% |
| Limonen | 0.050% |
| Colorant | 0.050% |
| CIT/MIT | 0.050% |

The invention claimed is:

1. An anhydro sugar alcohol n-nonanoic acid ester composition, comprising:

A) an anhydro sugar alcohol,

B) an anhydro sugar alcohol mono n-nonanoic ester, and

C) an anhydro sugar alcohol di n-nonanoic ester, wherein the anhydro sugar alcohol is at least one selected from the group consisting of sorbitan and xylitan.

2. The anhydro sugar alcohol n-nonanoic acid ester composition as claimed in claim 1, further comprising:

D) an anhydro sugar alcohol tri n-nonanoic ester, and/or

E) an anhydro sugar alcohol tetra n-nonanoic ester.

3. The anhydro alcohol n-nonanoic acid ester composition as claimed in claim 1, further comprising:

F) free n-nonanoic acid.

4. The anhydro sugar alcohol n-nonanoic acid ester composition as claimed in claim 1, wherein the anhydro sugar alcohol n-nonanoic acid ester has an average degree of esterification of 0.7 to 4.0.

5. The anhydro sugar alcohol n-nonanoic acid ester composition as claimed in claim 1, wherein the anhydro sugar alcohol n-nonanoic acid ester has a hydroxyl number of 50 to 600 mg KOH/g.

6. The anhydro sugar alcohol n-nonanoic acid ester composition as claimed in claim 1, wherein the anhydro sugar alcohol n-nonanoic acid ester has an acid value of 0.1 to 40 mg KOH/g.

7. The anhydro sugar alcohol n-nonanoic acid ester composition as claimed in claim 1, wherein the anhydro sugar alcohol n-nonanoic acid ester has a saponification value of 100 to 350 mg KOH/g.

8. The anhydro sugar alcohol n-nonanoic acid ester composition as claimed in claim 1, wherein the anhydro sugar alcohol n-nonanoic acid ester composition contains sorbitol n-nonanoic esters and/or xylitol n-nonanoic esters and a weight ratio of anhydro sugar alcohols to their corresponding sugar alcohols in the anhydro sugar alcohol n-nonanoic acid ester composition is greater than 60 to 40.

9. A method for the production of the anhydro sugar alcohol n-nonanoic acid ester composition as claimed in claim 1, wherein the anhydro sugar alcohol is at least one selected from the group consisting of sorbitan and xylitan, comprising:

I) providing sorbitol and/or xylitol,

II) dehydrating the sorbitol and/or xylitol to sorbitan and/or xylitan,

III) esterifying the sorbitan and/or xylitan with n-nonanoic acid, and optionally IV) isolating a formed anhydro sugar alcohol n-nonanoic acid ester composition from III).

10. A formulation, comprising the anhydro sugar alcohol n-nonanoic acid ester composition as claimed in claim 1, wherein the formulation comprises from 0.01% by weight to 10% by weight of the anhydro sugar alcohol n-nonanoic acid ester composition based on the total formulation.

11. The formulation according to claim 10, further comprising a surfactant.

12. A method of preventing and/or reducing deposits on dishes, glasses and cutlery from dishwashing processes, comprising:

treating dishes, glasses and cutlery with an aqueous composition, comprising the anhydro sugar alcohol n-nonanoic acid ester composition as claimed in claim 1.

13. The anhydro sugar alcohol n-nonanoic acid ester composition as claimed in claim 1, wherein the anhydro sugar alcohol n-nonanoic acid ester has an average degree of esterification of 0.8 to 2.5.

14. The anhydro sugar alcohol n-nonanoic acid ester composition as claimed in claim 1, wherein the anhydro sugar alcohol n-nonanoic acid ester has an average degree of esterification of 1.0 to 2.0.

15. The anhydro sugar alcohol n-nonanoic acid ester composition as claimed in claim 1, wherein the anhydro sugar alcohol n-nonanoic acid ester has a hydroxyl number of 100 to 550 mg KOH/g.

16. The anhydro sugar alcohol n-nonanoic acid ester composition as claimed in claim 1, wherein the anhydro sugar alcohol n-nonanoic acid ester has a hydroxyl number of 150 to 500 mg KOH/g.

17. The anhydro sugar alcohol n-nonanoic acid ester composition as claimed in claim 1, wherein the anhydro sugar alcohol n-nonanoic acid ester has an acid value of 0.5 to 30 mg KOH/g.

18. The anhydro sugar alcohol n-nonanoic acid ester composition as claimed in claim 1, wherein the anhydro sugar alcohol n-nonanoic acid ester has an acid value of 1 to 20 mg KOH/g.

19. The anhydro sugar alcohol n-nonanoic acid ester composition as claimed in claim 1, wherein the anhydro sugar alcohol n-nonanoic acid ester has a saponification value of 125 to 300 mg KOH/g.

20. The anhydro sugar alcohol n-nonanoic acid ester composition as claimed in claim 1, wherein the anhydro sugar alcohol n-nonanoic acid ester has a saponification value of 150 to 275 mg KOH/g.

* * * * *